(12) United States Patent
Iwai et al.

(10) Patent No.: US 9,888,901 B2
(45) Date of Patent: Feb. 13, 2018

(54) X-RAY DIAGNOSTIC APPARATUS AND X-RAY CT APPARATUS

(71) Applicant: Toshiba Medical Systems Corporation, Otawara-shi (JP)

(72) Inventors: Haruki Iwai, Toyonaka (JP); Amit Jain, Amherst, NY (US); Takuya Sakaguchi, Utsunomiya (JP); Seiichirou Nagai, Otawara (JP); Joseph Manak, Albany, NY (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 168 days.

(21) Appl. No.: 15/048,089

(22) Filed: Feb. 19, 2016

(65) Prior Publication Data

US 2017/0238896 A1 Aug. 24, 2017

(51) Int. Cl.

| | |
|---|---|
| *G01N 23/04* | (2006.01) |
| *A61B 6/00* | (2006.01) |
| *A61B 6/04* | (2006.01) |
| *A61B 6/03* | (2006.01) |

(52) U.S. Cl.
CPC ............ *A61B 6/542* (2013.01); *A61B 6/032* (2013.01); *A61B 6/0457* (2013.01); *A61B 6/4241* (2013.01)

(58) Field of Classification Search
CPC .. A61B 6/00; A61B 6/03; A61B 6/032; A61B 6/04; A61B 6/0457; A61B 6/4241; A61B 6/54; A61B 6/542; G01N 23/00; G01N 23/046; G01N 23/08; G01N 23/083; H05G 1/26; H05G 1/265; H05G 1/30; H05G 1/32; H05G 1/46
USPC ............... 378/4, 62, 101, 110, 112, 114, 116
See application file for complete search history.

(56) References Cited

U.S. PATENT DOCUMENTS

2011/0096905 A1 4/2011 Roessl et al.

FOREIGN PATENT DOCUMENTS

JP 2011-527223 10/2011

*Primary Examiner* — Jurie Yun
(74) *Attorney, Agent, or Firm* — Oblon, McClelland, Maier & Neustadt, L.L.P.

(57) ABSTRACT

An X-ray diagnostic apparatus according to an embodiment includes an X-ray tube, a detector, an acquisition circuitry, and imaging control circuitry. The acquisition circuitry creates photon count data indicating the number of photons of the X-rays incident on the detector, for each of a plurality of energy bins for identifying a plurality of target substances, based on the detection signal output by the detector. The imaging control circuitry determines an imaging plan including at least one of a setting condition that is a condition concerning setting of a plurality of energy bins used when the acquisition circuitry creates photon count data in main imaging, and an X-ray radiation condition that is a condition concerning X-rays emitted by the X-ray tube in main imaging, based on the photon count data created by the acquisition circuitry or image data of the subject.

29 Claims, 20 Drawing Sheets

| CASE NUMBER | Count-Bin1 | Count-Bin2 | Count-Bin3 | SETTING CONDITION |
|---|---|---|---|---|
| CASE 1 | L | L | L | KEEP |
| CASE 2 | H | L | L | KEEP |
| CASE 3 | L | H | L | KEEP |
| CASE 4 | L | L | H | KEEP |
| CASE 5 | L | H | H | "Bin1", "Bin4", "Bin5" |
| CASE 6 | H | L | H | "Bin6", "Bin7", "Bin5" |
| CASE 7 | H | H | L | "Bin6", "Bin7", "Bin5" |
| CASE 8 | H | H | H | "Bin8", "Bin5" |

| Count-Bin1 | Count-Bin2 | Count-Bin3 | X-RAY RADIATION CONDITION |
|---|---|---|---|
| H | H | H | KEEP |
| H | H | L | INCREASE TUBE VOLTAGE |
| H | L | H | INCREASE TUBE CURRENT |
| H | L | L | INCREASE TUBE VOLTAGE |
| L | H | H | REDUCE TUBE VOLTAGE |
| L | H | L | INCREASE TUBE CURRENT |
| L | L | H | REDUCE TUBE VOLTAGE |
| L | L | L | INCREASE TUBE CURRENT |

FIG.10

| Count-Bin1 | Count-Bin2 | Count-Bin3 | X-RAY RADIATION CONDITION |
|---|---|---|---|
| H | H | H | KEEP |
| H | H | L | INCREASE TUBE VOLTAGE |
| H | L | H | INCREASE TUBE CURRENT |
| H | L | L | INCREASE TUBE CURRENT |
| L | H | H | REDUCE TUBE VOLTAGE |
| L | H | L | INCREASE TUBE CURRENT |
| L | L | H | INCREASE TUBE CURRENT |
| L | L | L | INCREASE TUBE CURRENT |

FIG.11

| COUNT LEVEL | DETERMINATION CONDITION |
|---|---|
| L1 | $C < x \leq \alpha$, NUMBER OF ENERGY BINS: 1 |
| L2 | $x \leq C$, NUMBER OF ENERGY BINS: 1 |

FIG.12

| COUNT LEVEL | DETERMINATION CONDITION |
|---|---|
| L1 | $x < C_1$ |
| L2 | $C_1 \leq x < C_2$ |
| L3 | $C_2 \leq x < C_3$ |
| H1 | $C_3 \leq x < C_4$ |
| H2 | $C_4 \leq x$ |

FIG.13

| CRITERIA | X-RAY RADIATION CONDITION |
|---|---|
| ONE OR MORE L1 | TUBE CURRENT+0.5 mA |
| NO L1 AND ONE OR MORE L2 | TUBE CURRENT+0.2 mA |
| ONLY L3 | TUBE CURRENT+0.1 mA |

| TIME | X-RAY kV | X-RAY mA | (X0, Y0, X1, Y1) | TYPE |
|---|---|---|---|---|
| 0 | 90 | 100 | (0, 0, 1024, 1024) | 1 |
| 1 | 90 | 100 | (0, 0, 1024, 1024) | 1 |
| 2 | 90 | 100 | (0, 0, 1024, 1024) | 1 |
| ⋮ | ⋮ | ⋮ | ⋮ | ⋮ |
| ⋮ | ⋮ | ⋮ | ⋮ | ⋮ |
| ⋮ | ⋮ | ⋮ | ⋮ | ⋮ |
| N | 90 | 100 | (0, 0, 1024, 1024) | 1 |
| N+1 | 65 | 250 | (250, 250, 750, 750) | 2 |
| N+2 | 65 | 250 | (250, 250, 750, 750) | 2 |
| N+3 | 5 | 250 | (250, 250, 750, 750) | 2 |
| ⋮ | ⋮ | ⋮ | ⋮ | ⋮ |
| ⋮ | ⋮ | ⋮ | ⋮ | ⋮ |
| ⋮ | ⋮ | ⋮ | ⋮ | ⋮ |
| N+M | 65 | 250 | (250, 250, 750, 750) | 2 |

FIG.16

| CASE NUMBER | Count-Bin1 | Count-Bin2 | Count-Bin3 | SETTING CONDITION |
|---|---|---|---|---|
| CASE 9 | H | H | H | KEEP |
| CASE 10 | L | H | H | KEEP |
| CASE 11 | H | L | H | KEEP |
| CASE 12 | H | H | L | KEEP |
| CASE 13 | H | L | L | "Bin1", "Bin4", "Bin5" |
| CASE 14 | L | H | L | "Bin6", "Bin7", "Bin5" |
| CASE 15 | L | L | H | "Bin6", "Bin7", "Bin5" |
| CASE 16 | L | L | L | "Bin8", "Bin5" |

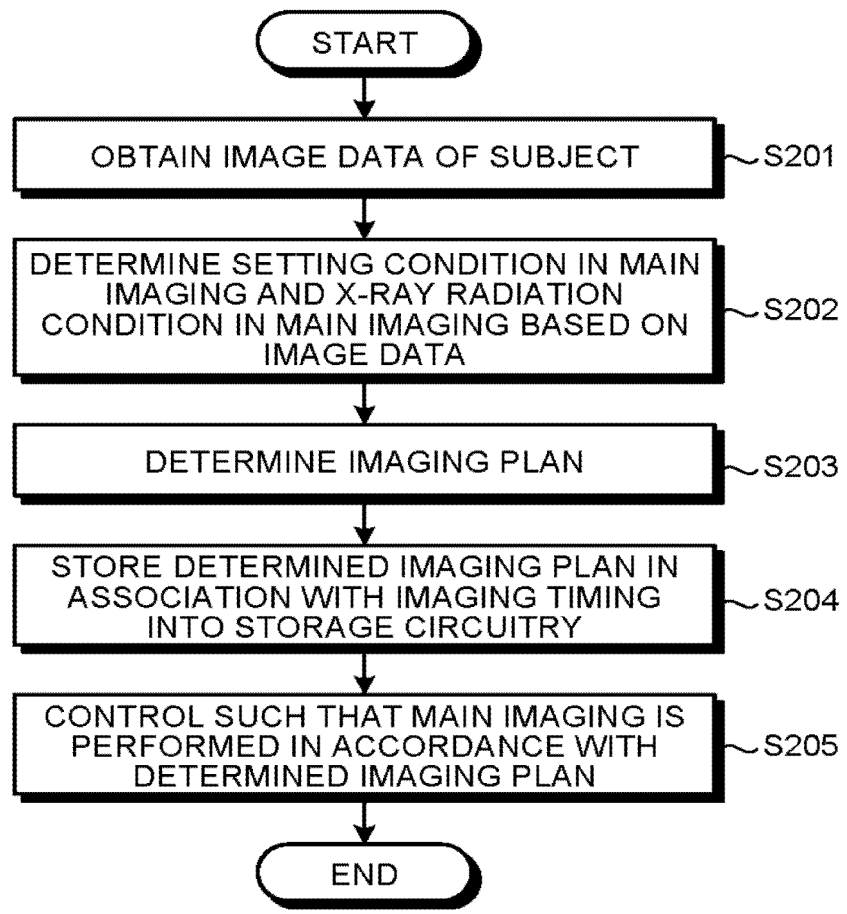

FIG.19

| Count-Bin1 | Count-Bin2 | Count-Bin3 | X-RAY RADIATION CONDITION |
|---|---|---|---|
| H1 | H | L | INCREASE TUBE VOLTAGE |
| H2 | H | L | INCREASE TUBE VOLTAGE + RADIATION QUALITY FILTER |

FIG.20

| BIN1; REGION 1 | BIN2; REGION 1 | BIN3; REGION 1 | BIN1; REGION 2 | BIN2; REGION 2 | BIN3; REGION 2 | X-RAY RADIATION CONDITION |
|---|---|---|---|---|---|---|
| H | H | L | H | H | L | INCREASE TUBE VOLTAGE |
| H | H | L | H | H | H | INCREASE TUBE VOLTAGE + REGION 2 BEAM LIMITING CONTROL |

FIG.21

| Count-Bin1 | Count-Bin2 | Count-Bin3 | X-RAY RADIATION CONDITION |
|---|---|---|---|
| H | H | H | KEEP |
| H | H | L | INCREASE TUBE VOLTAGE |
| H | L | H | INCREASE TUBE CURRENT |
| H | L | L | INCREASE TUBE CURRENT AND INCREASE TUBE VOLTAGE |
| L | H | H | REDUCE TUBE VOLTAGE |
| L | H | L | INCREASE TUBE CURRENT |
| L | L | H | INCREASE TUBE CURRENT AND REDUCE TUBE VOLTAGE |
| L | L | L | INCREASE TUBE CURRENT |

FIG.22

| X-RAY RADIATION CONDITION | PREDICTED COUNT Xi OF i-TH ENERGY BIN | CONSTRAINT CONDITION | OBJECTIVE FUNCTION |
|---|---|---|---|
| $(\delta V, \delta I)$<br>$\delta V$=VOLTAGE CHANGE AMOUNT<br>$\delta I$=CURRENT CHANGE AMOUNT | $X_i = C_i \times (1 + A_i \times \delta V + B_i \times \delta I)$ | $X_i \geq Th_i$ | MINIMIZE $P(\delta V, \delta I)$ |

FIG.23

| | | COUNT RATE | |
|---|---|---|---|
| | | H | L |
| COUNT | H | REDUCE TUBE VOLTAGE | REDUCE TUBE VOLTAGE AND INCREASE TUBE CURRENT |
| | L | REDUCE TUBE VOLTAGE | INCREASE TUBE CURRENT |

FIG.24

| CRITERIA | X-RAY RADIATION CONDITION AT PRESENT [mA] | X-RAY RADIATION CONDITION AFTER CHANGE [mA] |
|---|---|---|
| ONE OR MORE L1 | x | x+0.5 |
| NO L1 AND ONE OR MORE L2 | x | x+0.2 |
| ONLY L3 | x | x+0.1 |

X-RAY DIAGNOSTIC APPARATUS AND X-RAY CT APPARATUS

FIELD

Embodiments described herein relate generally to an X-ray diagnostic apparatus and an X-ray CT apparatus.

BACKGROUND

An X-ray diagnostic apparatus including a photon-counting detector can provide a high-contrast image of particular tissue (target substance) by creating count data based on a detection signal output from the photon-counting detector and performing a variety of image processing on the created count data.

In such an X-ray diagnostic apparatus, for example, photon count data indicating the number of photons in each of a plurality of energy bins of a particular kind is created based on a detection signal output from the photon-counting detector. A particular target substance that can be identified by the energy bins of the particular kind thus can be estimated with high precision. It is, however, difficult to estimate other target substances with high precision.

In an X-ray diagnostic apparatus, reduction in an exposure dose to a subject is also desired.

BRIEF DESCRIPTION OF THE DRAWINGS

FIG. 10 is a diagram schematically illustrating the X-ray radiation condition determination method according to a first modification to the first embodiment;

FIG. 11 is a diagram for explaining an example of a setting condition determination process according to a second modification to the first embodiment;

FIG. 12 is a diagram for explaining an example of an X-ray radiation condition determination process according to a fourth modification to the first embodiment;

FIG. 13 is a diagram for explaining an example of the X-ray radiation condition determination process according to the fourth modification to the first embodiment;

FIG. 16 is a diagram schematically illustrating the setting condition determination method according to a second embodiment;

FIG. 17 is a flowchart illustrating the procedure of the imaging control process executed by the imaging control circuitry according to a third embodiment;

FIG. 18 is a diagram for explaining an example of the imaging control process according to a fifth embodiment;

FIG. 19 is a diagram for explaining an example of the imaging control process according to the fifth embodiment;

FIG. 20 is a diagram for explaining an example of the imaging control process according to a sixth embodiment;

FIG. 21 is a diagram for explaining an example of the imaging control process according to a seventh embodiment;

FIG. 22 is a diagram for explaining a first modification to the seventh embodiment;

FIG. 23 is a diagram for explaining a second modification to the seventh embodiment;

FIG. 24 is a diagram for explaining an example of the imaging control process according to an eighth embodiment;

DETAILED DESCRIPTION

An X-ray diagnostic apparatus in an embodiment includes an X-ray tube, a detector, acquisition circuitry, and imaging control circuitry. The X-ray tube emits X-rays to a subject. The detector outputs a detection signal in response to incidence of the X-rays transmitted through the subject. The acquisition circuitry creates photon count data indicating the number of photons of the X-rays incident on the detector for each of a plurality of energy bins for identifying a plurality of target substances, based on the detection signal output by the detector. The imaging control circuitry determines an imaging plan including at least one of a setting condition that is a condition concerning setting of a plurality of energy bins used when the acquisition circuitry creates photon count data in main imaging, and an X-ray radiation condition that is a condition concerning X-rays emitted by the X-ray tube in main imaging, based on the photon count data created by the acquisition circuitry or image data of the subject, and performs control such that main imaging is performed in accordance with the determined imaging plan.

Embodiments of an X-ray diagnostic apparatus and an X-ray CT apparatus according to embodiments will be described in details below with reference to the accompanying drawings.

First Embodiment

Figure 1:
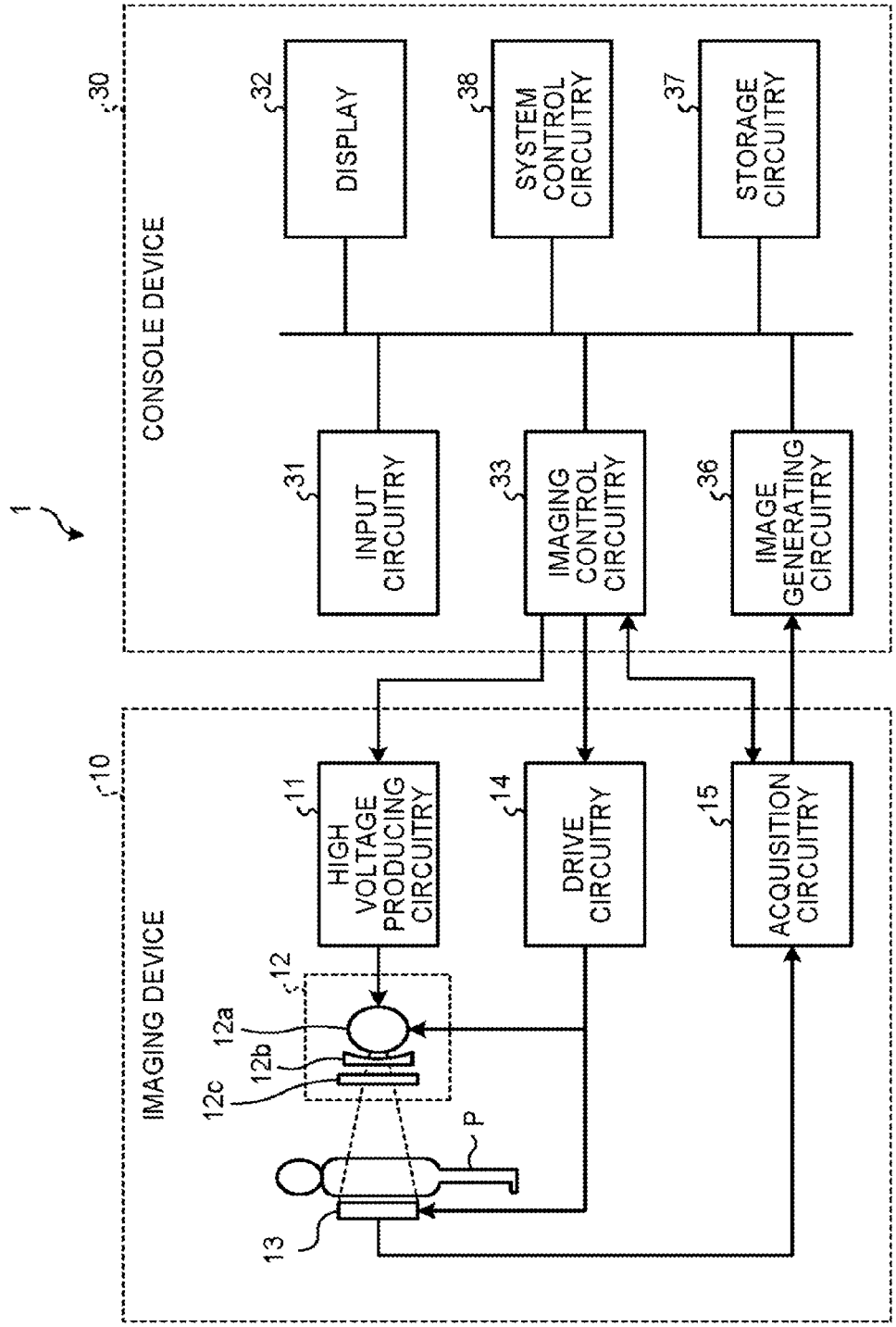
FIG. 1 is a diagram for explaining an example of the configuration of an X-ray diagnostic apparatus according to a first embodiment.

FIG. 1 is a block diagram illustrating a configuration example of an X-ray diagnostic apparatus according to a first embodiment.

This X-ray diagnostic apparatus 1 according to the first embodiment is a photon-counting general radiography system for taking a roentgenogram. As illustrated in FIG. 1, the X-ray diagnostic apparatus 1 has an imaging device 10 and a console device 30.

The imaging device 10 is a device that emits X-rays to a subject P and counts photons of X-rays transmitted through the subject P for each energy bin (energy band, energy section). The imaging device 10 has high voltage producing circuitry 11, a radiation device 12, a detector 13, drive circuitry 14, and acquisition circuitry 15.

The high voltage producing circuitry 11 supplies high voltage for allowing an X-ray tube 12a described later to produce X-rays. The high voltage producing circuitry 11 adjusts the amount of X-rays (X-ray dose) emitted to the subject P by adjusting tube voltage and tube current supplied to the X-ray tube 12a described later.

The radiation device 12 includes the X-ray tube 12a, a radiation quality filter 12b, and an X-ray beam limiting device 12c. The X-ray tube 12a produces X-rays to be emitted to the subject P with a high voltage supplied from the high voltage producing circuitry 11. For example, the X-ray tube 12a is a vacuum tube emitting X-rays. The radiation quality filter 12b is an X-ray filter for adjusting the X-ray dose of X-rays emitted from the X-ray tube 12a. For example, the radiation quality filter 12b is a filter that transmits and attenuates X-rays radiated from the X-ray tube 12a such that the X-rays emitted from the X-ray tube 12a to the subject P have a predetermined distribution. The radiation quality filter 12b may be called a wedge filter or a bow-tie filter. The X-ray beam limiting device 12c is a slit for limiting the radiation range of X-rays with an X-ray dose adjusted by the radiation quality filter 12b. For example, the X-ray beam limiting device 12c has four slidable blades, and these blades are slid to limit the X-rays produced by the X-ray tube 12a and apply the limited X-rays to the subject P. It is noted that the radiation range includes a region of interest (ROI).

The drive circuitry 14 moves the positions of the radiation device 12 and the detector 13, based on a control signal from the imaging control circuitry 33. The drive circuitry 14 also moves the radiation quality filter 12b to the front of the X-ray tube 12a or moves the radiation quality filter 12b from the front of the X-ray tube 12a, based on a control signal from the imaging control circuitry 33. The drive circuitry 14 also controls the X-ray beam limiting device 12c to change the size of the radiation range of X-rays emitted to the subject P or move the position of the radiation range, based on a control signal from the imaging control circuitry 33.

The detector 13 outputs a detection signal in response to incidence of X-rays emitted from the radiation device 12. The X-rays are, for example, X-rays transmitted through the subject P. The detector 13 has a plurality of detection elements for counting photons of X-rays (X-ray photons) transmitted through the subject P. The detector 13 is, for example, an X-ray flat panel detector including a plurality of detection elements regularly arranged in a predetermined direction and a direction crossing the predetermined direction. The detection elements each have a scintillator, a photodiode, and detection circuitry. The detection elements each convert photons of incident X-rays into light one by one with the scintillator and convert the light into electrical charge with the photodiode. The electric charge is converted by the detection circuitry into pulsed current. The detector 13, for example, outputs the pulsed current in the form of analog waveform data to the acquisition circuitry 15 or converts the pulsed current into digital waveform data to output the converted waveform data to the acquisition circuitry 15. Such waveform data is, for example, data of a waveform indicating a current value at each time, in which the time is represented by the horizontal axis and the current value is represented by the vertical axis. The detector 13 including a detection element having a scintillator and a photodiode as described above is called indirect conversion detector.

The detector 13 may be a direct conversion detector. The direct conversion detector is a detector that converts photons of X-rays incident on a detection element directly into electrical charge. When the detector 13 is a direct conversion detector, the detection element is, for example, a cadmium telluride (CdTe)-based semiconductor device. In addition, when the detector 13 is a direct conversion detector, the detector 13 converts electrical charge into pulsed current with the detection circuitry to output the pulsed current in the form of analog waveform data to the acquisition circuitry 15 or converts the pulsed current into digital waveform data to output the converted waveform data to the acquisition circuitry 15.

The detector 13 may be a detector having detection elements arranged in a row or a detector having detection elements arranged in a plurality of rows. In this case, in the X-ray diagnostic apparatus 1, a roentgenogram is taken while the drive circuitry 14 is moving the position of the detector 13 continuously or stepwise. It is noted that the aforementioned waveform data is an example of the detection signal.

The acquisition circuitry 15 and image generating circuitry 36 described later may be incorporated into the detector 13. In this case, the detector 13 has, in addition to the function of the detector 13 described above, the functions of the acquisition circuitry 15 and the image generating circuitry 36 described later. In this case, the detector 13, the acquisition circuitry 15, and the image generating circuitry 36 are integrated together.

The acquisition circuitry 15 is implemented by, for example, a data acquisition system (DAS). The acquisition circuitry 15 creates photon count data that is data indicating the count value of photons for each of a plurality of energy bins designated by the imaging control circuitry 33. For example, the acquisition circuitry 15 calculates, for each of the detection elements of the detector 13, energy of photons from the height of a peak of the waveform data, based on the waveform data output from the detection element. The acquisition circuitry 15 also counts, for each of the detection elements of the detector 13, pulses of the waveform data, based on the waveform data output from the detection element. The acquisition circuitry 15 then specifies an energy bin that includes the calculated energy, sets the count value of pulses as the number of photons in the specified energy bin, and registers the number of photons in the specified energy bin in a register. In this way, the acquisition circuitry 15 counts the number of photons of X-rays incident on a detection element, for each of a plurality of energy bins designated by the imaging control circuitry 33. That is, the acquisition circuitry 15 counts, for each detection element, photons of the incident X-rays for each of a plurality of energy bins.

The acquisition circuitry 15 then outputs, for each detection element, photon count data indicating the position of the detection element and the count value of photons for each of the plurality of energy bins designated by the imaging control circuitry 33 to the imaging control circuitry 33 and the image generating circuitry 36. For example, the acquisition circuitry 15 creates photon count data indicating the position of the detection element and the count value of photons for each of the plurality of energy bins and outputs the created photon count data to the imaging control circuitry 33 and the image generating circuitry 36.

For example, when the imaging control circuitry 33 designates a plurality of energy bins "Bin1", "Bin2", and "Bin3", the acquisition circuitry 15 outputs photon count data in the format (x, y, Count-Bin1, Count-Bin2, Count-Bin3) to the imaging control circuitry 33 and the image generating circuitry 36. Here, "x" is the value of the X coordinate when the position of a detection element on a predetermined plane in the detector 13 is represented by XY coordinates, and "y" is the value of the Y coordinate when the position of a detection element on a predetermined plane in the detector 13 is represented by XY coordinates. "Count-Bin1" is the count value of photons in energy bin "Bin1". Similarly, "Count-Bin2" is the count value of photons in energy bin "Bin2", and "Count-Bin3" is the count value of photons in energy bin "Bin3". When the position of the detector 13 is variable, the acquisition circuitry 15 may create, for each detection element, photon count data indicating the position of the detector 13 in addition to the position of the detection element and the count value of photons for each of a plurality of energy bins designated by the imaging control circuitry 33, and may output the created photon count data to the imaging control circuitry 33 and the image generating circuitry 36.

The process of creating photon count data in this manner is called an energy bin discrimination process.

The acquisition circuitry 15 has, for example, a pulse-height discriminator. Such a pulse-height discriminator can perform the process of creating photon count data using a plurality of energy bins by referring to a register in which a setting condition that is a condition concerning setting of a plurality of energy bins, is registered. When the imaging control circuitry 33 designates a plurality of energy bins, the pulse-height discriminator erases the past setting condition registered in the register and then registers a setting condition of the designated new energy bins in the register. The acquisition circuitry 15 thus can switch a plurality of energy bins to be used in performing the process of creating photon count data.

The acquisition circuitry 15 also reads photon count data from the register in a predetermined cycle and outputs the read photon count data to the imaging control circuitry 33 and the image generating circuitry 36. An example of the predetermined cycle is 1/100 seconds. For example, we will describe a case where, for a detection element at a position represented by the coordinates (x1,y1), the acquisition circuitry 15 reads photon count data (x1,y1,20,30,40) indicating that the count value of photons in energy bin "Bin1" is "20", the count value of photons in energy bin "Bin2" is "30", and the count value of photons in energy bin "Bin3" is "40", from the register, at a certain timing, and outputs the read photon count data (x1,y1,20,30,40) to the imaging control circuitry 33 and the image generating circuitry 36. In this case, in a period of time from that timing until 1/100 seconds has elapsed, when one photon of X-rays having energy included in energy bin "Bin1" is counted for the detection element at a position represented by the coordinates (x1,y1), photon count data (x1,y1,21,30,40) is registered in the register. At a timing when 1/100 seconds has elapsed since that timing, the acquisition circuitry 15 then reads out the photon count data (x1,y1,21,30,40) from the register and outputs the read photon count data (x1,y1,21,30,40) to the imaging control circuitry 33 and the image generating circuitry 36. In this manner, the acquisition circuitry 15 outputs photon count data in a predetermined cycle.

As described above, upon incidence of X-rays, the detector 13 converts a photon of the incident X-rays into an electrical signal. This electrical signal has a large value immediately after incidence of the photon and attenuates over time. By measuring the intensity, the attenuation rate, and the like of this electrical signal, the acquisition circuitry 15 can identify photons of the incident X-rays one by one and measure the energy thereof.

Unfortunately, when a current value of tube current of the X-ray tube 12a increases and the number of photons of the incident X-rays increases, before a photon of X-rays incident on the detector 13 is converted into an electrical signal and the electrical signal has attenuated, the next photon of X-rays enters and is converted into an electrical signal, which is then added to the value of the electrical signal derived from the initially incident photon of X-rays. This phenomenon is called pile-up. If pile-up occurs, the acquisition circuitry 15 erroneously makes a count as if a single photon having high energy enters, although a plurality of photons enter, so that the quality of an image generated by the console device 30 is degraded. In addition, if pile-up occurs, it is difficult to specify the peak position, and it is also difficult to accurately calculate energy of a photon because the height of a peak changes.

Under these circumstances, when the format of the waveform data output from the detector 13 is digital, the acquisition circuitry 15 performs a pulse decomposition process described below, before performing an energy bin discrimination process or during execution of an energy bin discrimination process, in order to reduce the effects of pile-up. That is, the acquisition circuitry 15 obtains a current value of a part of the waveform data that has pile-up, at appropriate time intervals, and specifies the boundaries of a plurality of peaks. The acquisition circuitry 15 then performs fitting on a plurality of peaks, based on the obtained current values and the specified boundaries of peaks.

The acquisition circuitry 15 then subtracts the fitting curves one by one from the part of the waveform data that has pile-up. In this way, the acquisition circuitry 15 can accurately perform counting of peaks of the waveform data and calculation of energy based on the heights of peaks.

The console device 30 is a device that accepts an operation by the operator and also generates an X-ray image using the photon count data created by the imaging device 10. As illustrated in FIG. 1, the console device 30 has input circuitry 31, a display 32, the imaging control circuitry 33, the image generating circuitry 36, storage circuitry 37, and system control circuitry 38.

The input circuitry 31 is implemented by a keyboard, a trackball, a switch, a button, a joystick, or the like. The input circuitry 31 accepts a variety of instructions and settings from the operator of the X-ray diagnostic apparatus 1 and transfers information of the instruction or the setting accepted from the operator to the system control circuitry 38.

For example, the input circuitry 31 accepts a setting condition described later and an X-ray radiation condition described later as well as an image processing condition for an X-ray image and transfers the accepted setting condition and X-ray radiation condition and image processing condition to the system control circuitry 38.

The display 32 is implemented by a liquid crystal monitor, a cathode ray tube (CRT) monitor, or the like, which is referred to by the operator. The display 32 is connected to the system control circuitry 38 to convert data of a variety of information and images sent from the system control circuitry 38 into an electrical signal for display and output the converted electrical signal. For example, the display 32 displays a roentgenogram to the operator or displays a graphical user interface (GUI) for accepting a variety of instructions, settings, and the like from the operator through the input circuitry 31, under the control by the system control circuitry 38. It is noted that the roentgenogram is an example of the X-ray image.

The imaging control circuitry 33 is implemented by, for example, a processor. The imaging control circuitry 33 controls the operation of the high voltage producing circuitry 11, the drive circuitry 14, and the acquisition circuitry 15 under the control of the system control circuitry 38 to control creation of photon count data in the imaging device 10. For example, the imaging control circuitry 33 controls the drive circuitry 14 to move the radiation device 12 and the detector 13 to a position suitable for taking a roentgenogram and controls the high voltage producing circuitry 11 to emit X-rays to the subject P. The imaging control circuitry 33 also controls the acquisition circuitry 15 to create a variety of photon count data, as will be described below.

The image generating circuitry 36 is implemented by, for example, a processor. The image generating circuitry 36 obtains photon count data output from the acquisition circuitry 15 and then generates a roentgenogram based on the obtained photon count data. The roentgenogram is used, for example, for diagnosis by a radiographer. For example, the image generating circuitry 36 generates a roentgenogram by performing a material decomposition process on photon count data. Such a roentgenogram is an image in which a target substance is identified.

As used herein, the "material decomposition process" is a process of identifying the kinds, atomic numbers, densities, and the like of substances included in the region in which a roentgenogram is taken, based on photon count data. The kinds, atomic numbers, densities, and the like of substances identified through such a material decomposition process are useful information for a radiographer to make a diagnosis.

As for algorithms of the material decomposition process performed by the image generating circuitry 36, various known algorithms for material decomposition can be applied. For example, when photon count data created using N energy bins is used, such an algorithm for the material decomposition process can generate a roentgenogram in which N target substances as many as the number of energy bins are identified.

The image generating circuitry 36 then outputs the generated roentgenogram to the storage circuitry 37.

The storage circuitry 37 is implemented by, for example, a semiconductor memory device such as a random access memory (RAM) and a flash memory, a hard disk, an optical disk, or the like. The storage circuitry 37 stores the roentgenogram output from the image generating circuitry 36.

The system control circuitry 38 is implemented by, for example, a processor. The system control circuitry 38 controls the photon-counting X-ray diagnostic apparatus 1 by controlling the operation of the imaging device 10 and the console device 30. For example, the system control circuitry 38 controls creation of photon count data in the imaging device 10 by controlling the imaging control circuitry 33 and controls generation and display of a roentgenogram by controlling the console device 30.

As used in the description, the term "processor" means, for example, a central processing unit (CPU), a graphics processing unit (GPU), or circuitry such as an application specific integrated circuit (ASIC) or a programmable logic device (for example, a simple programmable logic device (SPLD), a complex programmable logic device (CPLD), and a field programmable gate array (FPGA)). In place of storing a program in an internal storage circuitry, a program may be directly built in a circuitry in the processor. In this case, the processor reads out and executes the program built in the circuitry to implement the functions.

An example of the operation of the imaging control circuitry 33 will now be described. We will describe, for example, a case where there are four substances to be identified (target substances) in the X-ray diagnostic apparatus 1, and the number of energy bins in the energy bin discrimination process executed by the acquisition circuitry 15 is equal to or smaller than three. However, the kinds of target substances and the number of energy bins are not limited thereto. For example, in the following description, when an iodine-based contrast medium and a gadolinium-based contrast medium are administered to a subject P and a brain blood vessel of the subject P is treated with a Pt structure, four target substances are identified, namely, iodine included in the iodine-based contrast medium, gadolinium included in the gadolinium-based contrast medium, platinum included in the Pt structure, and the skull of the subject P. Examples of the Pt structure include a stent, a guide wire, a coil, and a marker. In place of the Pt structure, nanoparticles (micro bubble coating) may be administered as a contrast medium to the subject P. In this case, nanoparticles are a target substance.

Figure 2:
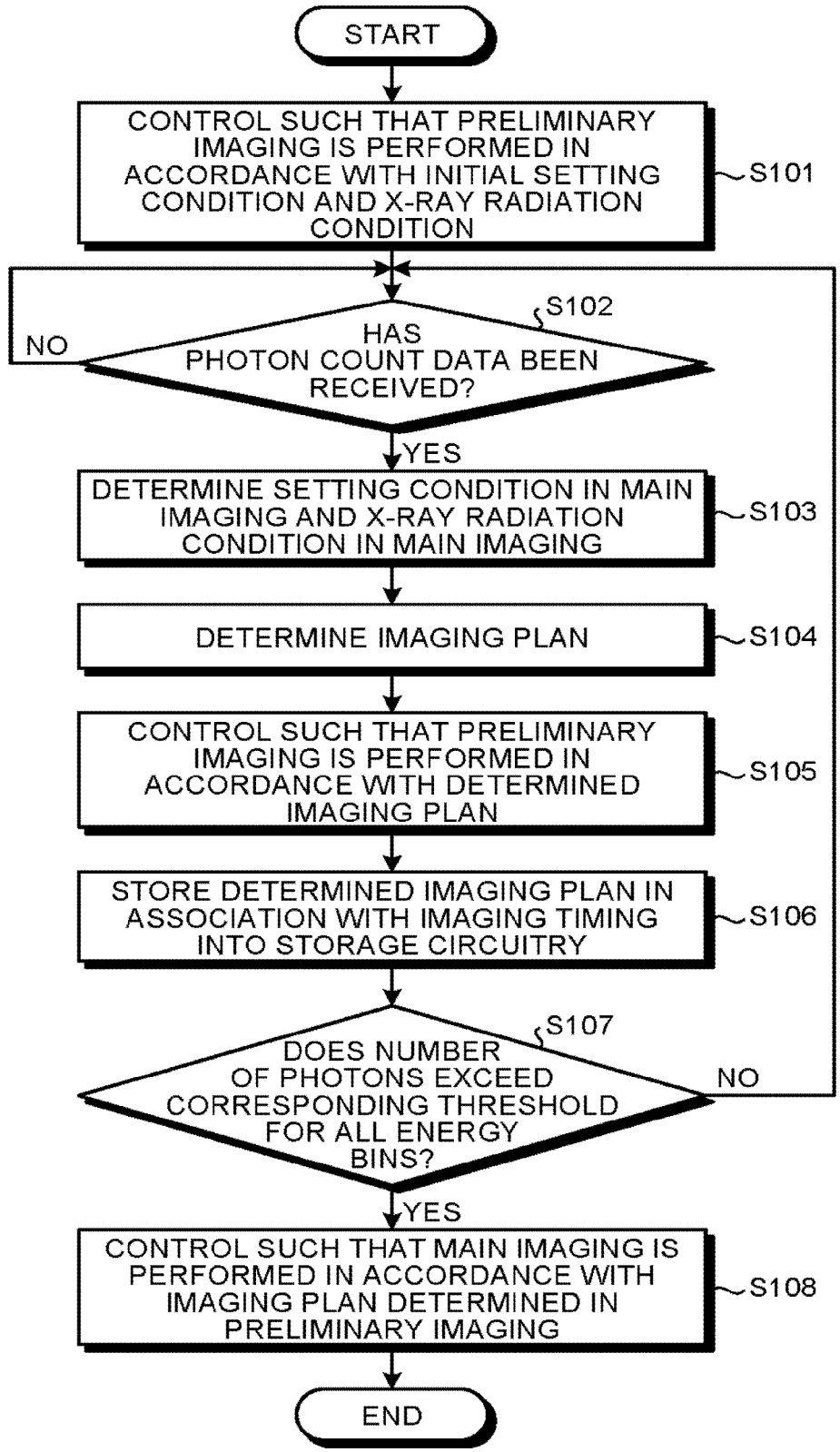
FIG. 2 is a flowchart illustrating the procedure of an imaging control process executed by imaging control circuitry according to the first embodiment.

As described above, the imaging control circuitry 33 controls creation of photon count data in the imaging device 10 by controlling the operation of the acquisition circuitry 15. FIG. 2 is a flowchart illustrating the procedure of an imaging control process executed by the imaging control circuitry according to the first embodiment. This imaging control process is executed when the input circuitry 31 accepts a setting condition and an X-ray radiation condition from the user and the imaging control circuitry 33 receives the accepted setting condition and X-ray radiation condition. As used herein, the "setting condition" is, for example, a condition concerning setting of a plurality of energy bins used when the acquisition circuitry 15 creates photon count data. The "X-ray radiation condition" is, for example, a condition concerning X-rays emitted by the radiation device 12. The accepted setting condition is a condition initially (at the start of control) used in controlling the acquisition circuitry 15 in each of preliminary imaging and main imaging.

The accepted X-ray radiation condition is a condition initially (at the start of control) used in controlling the high voltage producing circuitry 11 and the drive circuitry 14 in each of preliminary imaging and main imaging. The accepted setting condition and X-ray radiation condition therefore may be referred to as initial setting condition and X-ray radiation condition in each of preliminary imaging and main imaging.

As illustrated in the example in FIG. 2, the imaging control circuitry 33 controls the high voltage producing circuitry 11, the drive circuitry 14, and the acquisition circuitry 15 so as to perform preliminary imaging prior to main imaging, in accordance with the initial setting condition and X-ray radiation condition (step S101).

For example, at step S101, the imaging control circuitry 33 outputs an instruction to the high voltage producing circuitry 11 to adjust the tube voltage, tube current, and the like of the X-ray tube 12a to the tube voltage, tube current, and the like indicated by the initial X-ray radiation condition. The high voltage producing circuitry 11 then adjusts the tube voltage, tube current, and the like of the X-ray tube 12a to the tube voltage, tube current, and the like indicated by the initial X-ray radiation condition.

At step S101, the imaging control circuitry 33 sets a plurality of energy bins indicated by the initial setting condition as a plurality of energy bins to be used in executing an energy bin discrimination process and outputs an instruction to execute an energy bin discrimination process to the acquisition circuitry 15. The acquisition circuitry 15 then sets a plurality of energy bins in which photons are counted in the energy bin discrimination process to a plurality of energy bins indicated by the initial setting condition and executes an energy bin discrimination process. The acquisition circuitry 15 then outputs the generated photon count data to the imaging control circuitry 33 and the like.

The imaging control circuitry 33 then determines whether the photon count data output from the acquisition circuitry 15 has been received, in preliminary imaging (step S102). If the photon count data has not been received (No at step S102), the imaging control circuitry 33 performs the processing at step S102 again. On the other hand, if the photon count data has been received (Yes at step S102), the imaging control circuitry 33 performs the processing described below. That is, the imaging control circuitry 33 determines a setting condition in main imaging and an X-ray radiation condition in main imaging, based on the received photon count data (step S103).

The imaging control circuitry 33 then determines an imaging plan including the determined setting condition and X-ray radiation condition (step S104).

The imaging control circuitry 33 may determine a setting condition alone, between a setting condition in main imaging and an X-ray radiation condition in main imaging, at step S103, and determine an imaging plan including the determined setting condition, at step S104. Alternatively, the imaging control circuitry 33 may determine an X-ray radiation condition alone, between a setting condition in main imaging and an X-ray radiation condition in main imaging, at step S103, and determine an imaging plan including the determined X-ray radiation condition, at step S104. That is, the imaging control circuitry 33 may determine at least one of a setting condition in main imaging and an X-ray radiation condition in main imaging, at step S103, and determine an imaging plan including the determined at least one of a setting condition in main imaging and an X-ray radiation condition in main imaging, at step S104. This is applicable to other embodiments described later.

The imaging control circuitry 33 then controls the high voltage producing circuitry 11, the drive circuitry 14, and the acquisition circuitry 15 so as to perform preliminary imaging in accordance with the determined imaging plan (step S105).

The imaging control circuitry 33 then stores the determined imaging plan, in association with the timing of starting imaging with the determined imaging plan (imaging timing), into the storage circuitry 37 (step S106). As used herein, the "imaging timing" is, for example, a period of time from the timing of starting preliminary imaging to the timing when the high voltage producing circuitry 11, the drive circuitry 14, and the acquisition circuitry 15 are controlled such that preliminary imaging is performed in accordance with the determined imaging plan. The "timing of starting preliminary imaging" refers to, for example, a timing when the high voltage producing circuitry 11, the drive circuitry 14, and the acquisition circuitry 15 are controlled such that preliminary imaging is performed in accordance with the initial imaging plan in preliminary imaging at step S101 described above.

The imaging control circuitry 33 then determines whether the number of photons exceeds a corresponding threshold described later, for all of the energy bins (step S107). If the number of photons exceeds the corresponding threshold for all of the energy bins (Yes at step S107), it can be assumed that the number of photons necessary for creating one roentgenogram is obtained in all of the energy bins. The imaging control circuitry 33 therefore terminates preliminary imaging and proceeds to the next step S108. On the other hand, if the number of photons does not exceed the corresponding threshold for at least one energy bin of all the energy bins (No at step S107), the process returns to step S102. In this manner, preliminary imaging is performed until the number of photons necessary for creating one roentgenogram is obtained for all of the energy bins.

That is, every time photon count data is received, the imaging control circuitry 33 determines a setting condition in main imaging and an X-ray radiation condition in main imaging, based on the received photon count data, at step S103. Here, the time intervals at which photon count data is received are the same as the predetermined cycles described above. Every time a setting condition in main imaging and an X-ray radiation condition in main imaging are determined, the imaging control circuitry 33 determines an imaging plan at step S104. Every time an imaging plan is determined, the imaging control circuitry 33 controls the high voltage producing circuitry 11, the drive circuitry 14, and the acquisition circuitry 15 so as to perform preliminary imaging in accordance with the determined imaging plan at step S105. Every time control is performed so as to perform preliminary imaging, the imaging control circuitry 33 stores the determined imaging plan in association with the imaging timing into the storage circuitry 37 at step S106.

Through the processing at steps S101 to S107 as described above, an imaging plan in main imaging in creating one roentgenogram is determined in preliminary imaging.

For example, we will describe a case where control is performed so as to perform preliminary imaging in accordance with the initial imaging plan described above; imaging plan A is determined based on the photon count data obtained through preliminary imaging with the initial imaging plan; control is performed so as to perform preliminary imaging in accordance with imaging plan A; imaging plan B is determined based on the photon count data obtained through the preliminary imaging with the imaging plan A; control is performed so as to perform preliminary imaging in accordance with imaging plan B; imaging plan C is determined based on the photon count data obtained through the preliminary imaging with imaging plan B; and control is performed so as to perform preliminary imaging in accordance with imaging plan C. It is assumed that a period of time from the start of preliminary imaging until control is performed so as to perform preliminary imaging in accordance with imaging plan A is 0.01 seconds. It is also assumed that a period of time from the start of preliminary imaging until control is performed so as to perform preliminary imaging in accordance with imaging plan B is 0.02 seconds. It is also assumed that a period of time from the start of preliminary imaging until control is performed so as to perform preliminary imaging in accordance with imaging plan C is 0.03 seconds. In this case, the imaging control circuitry 33 stores 0.01 seconds in association with imaging plan A into the storage circuitry 37. The imaging control circuitry 33 also stores 0.02 seconds in association with imaging plan B into the storage circuitry 37. The imaging control circuitry 33 also stores 0.03 seconds in association with imaging plan C into the storage circuitry 37.

When the number of photons necessary for creating one roentgenogram is obtained in all of the energy bins, the imaging control circuitry 33 controls the high voltage producing circuitry 11, the drive circuitry 14, and the acquisition circuitry 15 so as to perform main imaging. In doing so, the imaging control circuitry 33 controls the high voltage producing circuitry 11, the drive circuitry 14, and the acquisition circuitry 15 such that main imaging is performed in accordance with the imaging plan determined in the preliminary imaging (step S108). The imaging control process then ends.

For example, we will describe a case where 0.01 seconds in association with imaging plan A, 0.02 seconds in association with imaging plan B, and 0.03 seconds in association with imaging plan C are stored in the storage circuitry 37 in preliminary imaging. In this case, in main imaging, first, the imaging control circuitry 33 reads these pieces of information from the storage circuitry 37. The imaging control circuitry 33 then controls the high voltage producing circuitry 11, the drive circuitry 14, and the acquisition circuitry 15 so as to perform main imaging in accordance with the initial imaging plan. Next, the imaging control circuitry 33 controls the high voltage producing circuitry 11, the drive circuitry 14, and the acquisition circuitry 15 such that main imaging is performed in accordance with imaging plan A at a timing when 0.01 seconds has elapsed since the start of main imaging. Next, the imaging control circuitry 33 controls the high voltage producing circuitry 11, the drive circuitry 14, and the acquisition circuitry 15 such that main imaging is performed in accordance with imaging plan B at a timing when 0.02 seconds has elapsed since the start of main imaging. The imaging control circuitry 33 then controls the high voltage producing circuitry 11, the drive circuitry 14, and the acquisition circuitry 15 such that main imaging is performed in accordance with imaging plan C at a timing when 0.03 seconds has elapsed since the start of main imaging.

The image generating circuitry 36 generates a roentgenogram by performing a material decomposition process on the photon count data obtained through main imaging. The generated roentgenogram appears on, for example, the display 32 under the control of the system control circuitry 38.

Figure 3:
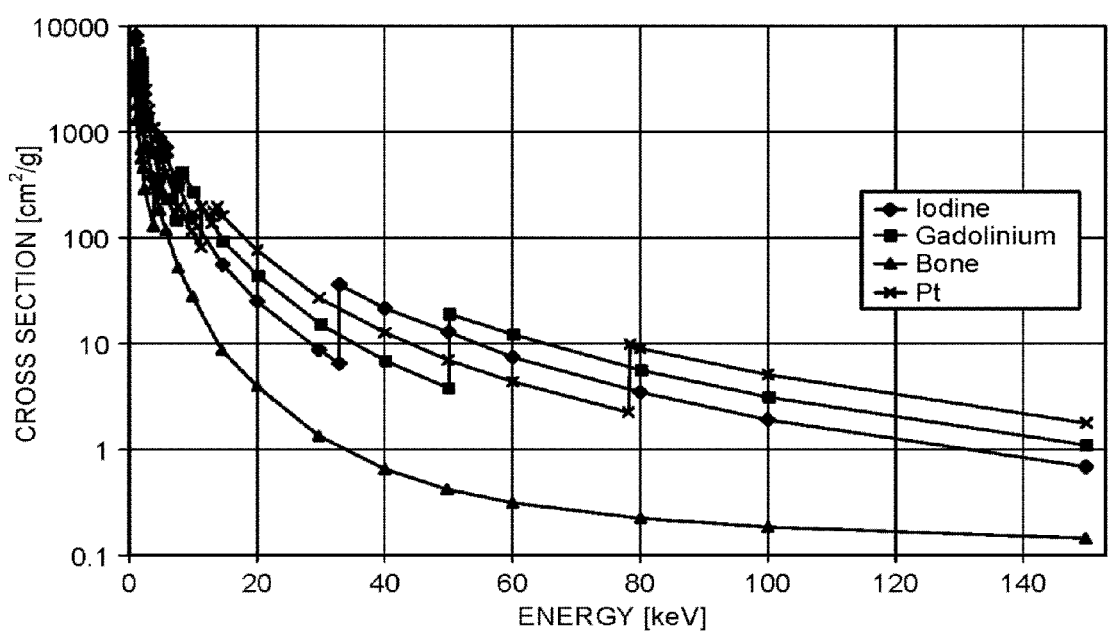
FIG. 3 is a graph illustrating an example of the relation between incident X-ray energy and cross section of each of four target substances.
Figures 4, 5:
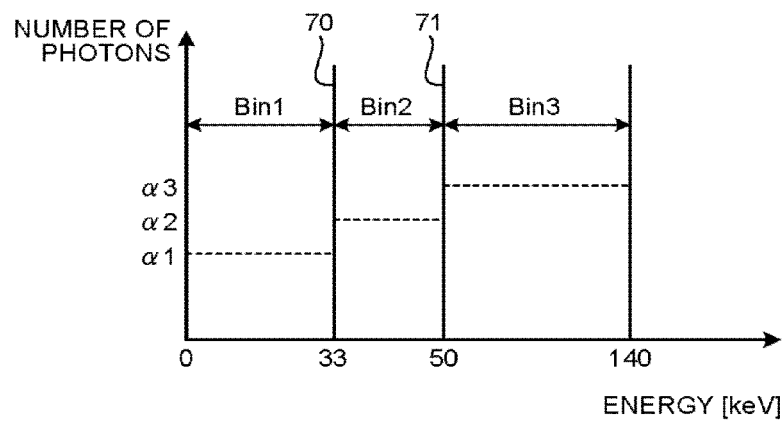
FIG. 4 is a diagram illustrating an example of a plurality of energy bins.
FIG. 5 is a diagram schematically illustrating a setting condition determination method.

An example of a setting condition determination method for determining a setting condition will now be described. Referring to FIG. 3 to FIG. 8, a description will be given with a specific example. FIG. 3 is a graph illustrating an example of the relation between incident X-ray energy and cross section of each of the four target substances. FIG. 4 and FIG. 6 to FIG. 8 are diagrams illustrating examples of a plurality of energy bins. FIG. 5 is a diagram schematically illustrating the setting condition determination method.

In the graph illustrated in FIG. 3, the horizontal axis represents the magnitude of incident X-ray energy, and the vertical axis represents the size of cross section. As illustrated in FIG. 3, in iodine included in the iodine-based contrast medium, the cross section abruptly changes discontinuously when the incident X-ray radiation energy is about 33 keV. Iodine, therefore, is a substance in which the absorption coefficient of X-rays changes discontinuously when the incident energy is about 33 keV. That is, the absorption edge of iodine is about 33 keV. In gadolinium included in the gadolinium-based contrast medium, the cross section abruptly changes discontinuously when the incident X-ray radiation energy is about 50 keV. Gadolinium, therefore, is a substance in which the absorption coefficient of X-rays changes discontinuously when the incident energy is about 50 keV. That is, the absorption edge of gadolinium is about 50 keV. In platinum (Pt) included in the Pt structure, the cross section abruptly changes discontinuously when the incident X-ray radiation energy is about 80 keV. Platinum, therefore, is a substance in which the absorption coefficient of X-rays changes discontinuously when the incident energy is about 80 keV. That is, the absorption edge of platinum is about 80 keV. In the skull (Bone) of the subject P, the cross section changes gradually when the incident energy is from 0 keV to 140 keV. The skull of the subject P, therefore, is a substance in which the absorption coefficient of X-rays changes gradually when the incident energy is from 0 keV to 140 keV.

FIG. 4 illustrates an example of the initial setting condition. The initial setting condition illustrated in FIG. 4 indicates energy bin "Bin1", energy bin "Bin2", and energy bin "Bin3" used when an energy bin discrimination process is executed. That is, in preliminary imaging, first, the imaging control circuitry 33 sets energy bin "Bin1", energy bin "Bin2", and energy bin "Bin3" as a plurality of energy bins used in executing an energy bin discrimination process, in accordance with the initial setting condition, and outputs an instruction to execute an energy bin discrimination process to the acquisition circuitry 15. A plurality of energy bins illustrated in FIG. 4 will now be described. As illustrated in FIG. 4, a plurality of energy bins are set by dividing the energy bin in a range of 0 keV to 140 keV by a threshold 70 corresponding to the absorption edge "33 keV" of iodine and a threshold 71 corresponding to the absorption edge "50 keV" of gadolinium. Energy bin "Bin1" is an energy bin in a range of 0 keV or more to less than 33 keV. Energy bin "Bin2" is an energy bin in a range of 33 keV or more to less than 50 keV. Energy bin "Bin3" is an energy bin in a range of 50 keV or more to less than 140 keV.

Thresholds $\alpha 1$, $\alpha 2$, and $\alpha 3$ are set for energy bin "Bin1", energy bin "Bin2", and energy bin "Bin3", respectively, as illustrated in FIG. 4. When the image generating circuitry 36 performs a material decomposition process on the photon count data created through the energy bin discrimination process using energy bin "Bin1", energy bin "Bin2", and energy bin "Bin3", three target substances, namely, "Iodine", "Gadolinium", "Bone" are identified through the material decomposition process. Specifically, when the number of counted photons (the average of the numbers of photons in the region of interest in energy bin "Bin1") is greater than threshold $\alpha 1$ in energy bin "Bin1", the number of counted photons (the average of the numbers of photons in the region of interest in energy bin "Bin2") is greater than threshold $\alpha 2$ in energy bin "Bin2", and the number of counted photons (the average of the numbers of photons in the region of interest in energy bin "Bin3") is greater than threshold $\alpha 3$ in energy bin "Bin3", the target substances "Iodine", "Gadolinium", and "Bone" can be identified through the material decomposition process. A plurality of energy bins "Bin1", "Bin2", and "Bin3" are for identifying three target substances, namely, "Iodine", "Gadolinium", and "Bone".

It is noted that the average of the numbers of photons (count values) in the region of interest in energy bin "Bin N (N=1, 2, . . . )" refers to the average of the numbers of photons of a plurality of detection elements in the region of interest in energy bin "BinN". A plurality of energy bins "Bin1", "Bin2", and "Bin3" is an example of a first plurality of energy bins.

Upon receiving the instruction described above, the acquisition circuitry 15 sets a plurality of energy bins in which photons are counted, to energy bin "Bin1", energy bin "Bin2", and energy bin "Bin3", and executes an energy bin discrimination process. That is, the acquisition circuitry 15 creates, for each detection element, photon count data that is data indicating the count value of photons for each of energy bin "Bin1", energy bin "Bin2", and energy bin "Bin3" designated by the imaging control circuitry 33. Such photon count data is an example of the first photon count data. The acquisition circuitry 15 then outputs the generated photon count data to the imaging control circuitry 33.

Upon receiving the photon count data, the imaging control circuitry 33 performs the following processing. That is, the imaging control circuitry 33 determines whether the average "Count-Bin1" of the numbers of photons in the region of interest in energy bin "Bin1" indicated by the photon count data exceeds threshold $\alpha 1$, determines whether the average "Count-Bin2" of the numbers of photons in energy bin "Bin2" indicated by the photon count data exceeds threshold $\alpha 2$, and determines whether the average "Count-Bin3" of the numbers of photons in energy bin "Bin3" indicated by the photon count data exceeds threshold $\alpha 3$.

Case 1

A case where the imaging control circuitry 33 determines that the average "Count-Bin1" of the numbers of photons is equal to or smaller than threshold $\alpha 1$, the average "Count-Bin2" of the numbers of photons is equal to or smaller than threshold $\alpha 2$, and the average "Count-Bin3" of the numbers of photons is equal to or smaller than threshold $\alpha 3$ will be described (Case 1). In this case, it can be assumed that photons are not counted as many as all the three target substances "Iodine", "Gadolinium", and "Bone" can be identified through the material decomposition process executed by the image generating circuitry 36. As illustrated in FIG. 5, the imaging control circuitry 33 determines a setting condition for allowing the acquisition circuitry 15 to keep a plurality of energy bins in which photons are counted, as it is, for example, a setting condition for setting present energy bin "Bin1", energy bin "Bin2", and energy bin "Bin3". The imaging control circuitry 33 then controls the acquisition circuitry 15 so as to perform preliminary imaging in accordance with the determined setting condition. The acquisition circuitry 15 thus keeps energy bin "Bin1", energy bin "Bin2", and energy bin "Bin3" at present. In FIG. 5, "L" denotes being equal to or smaller than a corresponding threshold, and "H" denotes exceeding a corresponding threshold. The imaging control circuitry 33 then stores the imaging plan including the determined setting condition in association with the imaging timing into the storage circuitry 37.

Case 2

A case where the imaging control circuitry 33 determines that the average "Count-Bin1" of the numbers of photons exceeds threshold $\alpha 1$, the average "Count-Bin2" of the numbers of photons is equal to or smaller than threshold $\alpha 2$, and the average "Count-Bin3" of the numbers of photons is equal to or smaller than threshold $\alpha 3$ will be described (Case 2). Also in this case, it can be assumed that photons are not counted as many as all of the three target substances "Iodine", "Gadolinium", and "Bone" can be identified through the material decomposition process executed by the image generating circuitry 36. The imaging control circuitry 33 therefore determines a setting condition for allowing the acquisition circuitry 15 to keep a plurality of energy bins in which photons are counted, as it is, as illustrated in FIG. 5. The imaging control circuitry 33 then controls the acquisition circuitry 15 so as to perform preliminary imaging in accordance with the determined setting condition. The imaging control circuitry 33 then stores the imaging plan including the determined setting condition in association with the imaging timing into the storage circuitry 37.

Case 3

A case where the imaging control circuitry 33 determines that the average "Count-Bin1" of the numbers of photons is equal to or smaller than threshold $\alpha 1$, the average "Count-Bin2" of the numbers of photons exceeds threshold $\alpha 2$, and the average "Count-Bin3" of the numbers of photons is equal to or smaller than threshold $\alpha 3$ will be described (Case 3). Also in this case, it can be assumed that photons are not counted as many as all of the three target substances "Iodine", "Gadolinium", and "Bone" can be identified through the material decomposition process executed by the image generating circuitry 36. The imaging control circuitry 33 therefore determines a setting condition for allowing the acquisition circuitry 15 to keep a plurality of energy bins in which photons are counted, as it is, as illustrated in FIG. 5. The imaging control circuitry 33 then controls the acquisition circuitry 15 so as to perform preliminary imaging in accordance with the determined setting condition. The imaging control circuitry 33 then stores the imaging plan including the determined setting condition in association with the imaging timing into the storage circuitry 37.

Case 4

A case where the imaging control circuitry 33 determines that the average "Count-Bin1" of the numbers of photons is equal to or smaller than threshold $\alpha 1$, the average "Count-Bin2" of the numbers of photons is equal to or smaller than threshold $\alpha 2$, and the average "Count-Bin3" of the numbers of photons exceeds threshold $\alpha 3$ will be described (Case 4). Also in this case, it can be assumed that photons are not counted as many as all of the three target substances "Iodine", "Gadolinium", and "Bone" can be identified through the material decomposition process executed by the image generating circuitry 36. The imaging control circuitry 33 therefore determines a setting condition for allowing the acquisition circuitry 15 to keep a plurality of energy bins in which photons are counted, as it is, as illustrated in FIG. 5. The imaging control circuitry 33 then controls the acquisition circuitry 15 so as to perform preliminary imaging in accordance with the determined setting condition. The imaging control circuitry 33 then stores the imaging plan including the determined setting condition in association with the imaging timing into the storage circuitry 37.

Case 5

Figure 6:
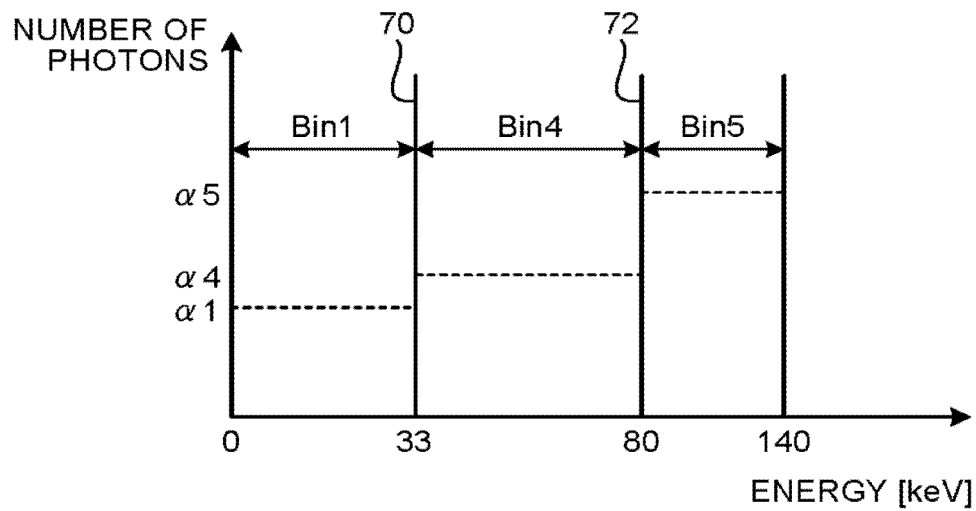
FIG. 6 is a diagram illustrating an example of a plurality of energy bins.

A case where it is determined that the average "Count-Bin1" of the numbers of photons is equal to or smaller than threshold $\alpha 1$, the average "Count-Bin2" of the numbers of photons exceeds threshold $\alpha 2$, and the average "Count-Bin3" of the numbers of photons exceeds threshold $\alpha 3$ will be described (Case 5). In this case, the imaging control circuitry 33 determines a setting condition for switching (setting) a plurality of energy bins in which photons are counted in an energy bin discrimination process to a plurality of energy bins "Bin1", "Bin4", and "Bin5" as illustrated in FIG. 6. A threshold 72 in FIG. 6 corresponds to the absorption edge "80 keV" of platinum. The imaging control circuitry 33 then controls the acquisition circuitry 15 so as to perform preliminary imaging in accordance with the determined setting condition. The acquisition circuitry 15 thus switches a plurality of energy bins in which photons are counted in an energy bin discrimination process to energy bin "Bin1", energy bin "Bin4", and energy bin "Bin5" and executes an energy bin discrimination process. That is, the acquisition circuitry 15 creates, for each detection element, photon count data that is data indicating a count value of photons for each of energy bin "Bin1", energy bin "Bin4", and energy bin "Bin5" designated by the imaging control circuitry 33, and outputs the created photon count data to the imaging control circuitry 33 and the like. Such photon count data is an example of the second photon count data. The imaging control circuitry 33 then stores the imaging plan including the determined setting condition in association with the imaging timing into the storage circuitry 37.

Thresholds $\alpha 1$, $\alpha 4$, and $\alpha 5$ are set for energy bin "Bin1", energy bin "Bin4", and energy bin "Bin5", respectively. When the image generating circuitry 36 performs a material decomposition process on the photon count data created through the energy bin discrimination process using energy bin "Bin1", energy bin "Bin4", and energy bin "Bin5", three target substances "Iodine", "Bone", and "Platinum" are identified through the material decomposition process. Specifically, when the number of counted photons (the average of the numbers of photons in the region of interest in energy bin "Bin1") is greater than threshold $\alpha 1$ in energy bin "Bin1", the number of counted photons (the average of the numbers of photons in the region of interest in energy bin "Bin4") is greater than threshold $\alpha 4$ in energy bin "Bin4", and the number of counted photons (the average of the numbers of photons in the region of interest in energy bin "Bin5") is greater than threshold $\alpha 5$ in energy bin "Bin5", target substances "Iodine", "Bone", and "Platinum" can be identified through the material decomposition process. A plurality of energy bins "Bin1", "Bin4", and "Bin5" is therefore for identifying three target substances "Iodine", "Bone", and "Platinum". A plurality of energy bins "Bin1", "Bin4", and "Bin5" is an example of a second plurality of energy bins.

Case 6

Figure 7:
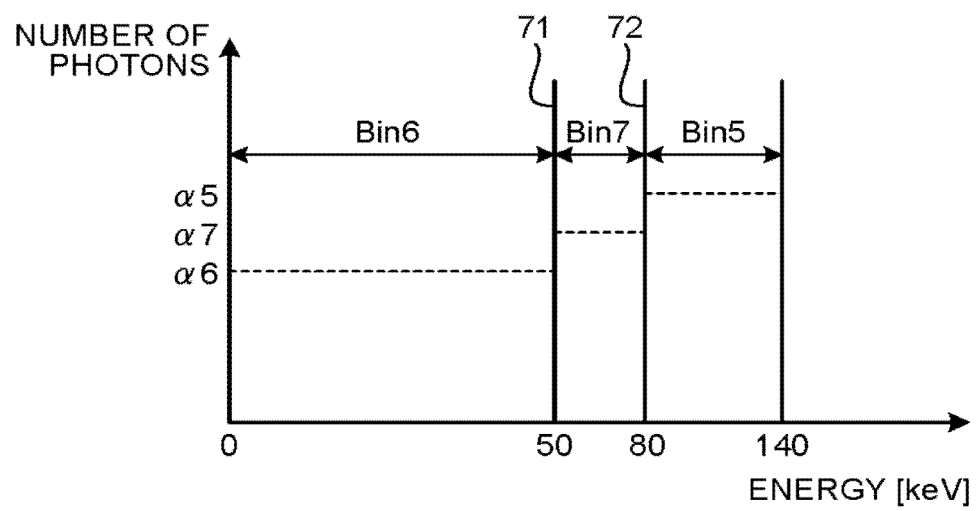
FIG. 7 is a diagram illustrating an example of a plurality of energy bins.

A case where it is determined that the average "Count-Bin1" of the numbers of photons exceeds threshold $\alpha 1$, the average "Count-Bin2" of the numbers of photons is equal to or smaller than threshold $\alpha 2$, and the average "Count-Bin3" of the numbers of photons exceeds threshold $\alpha 3$ will be described (Case 6). In this case, the imaging control circuitry 33 determines a setting condition for switching a plurality of energy bins in which photons are counted in an energy bin discrimination process to a plurality of energy bins "Bin6", "Bin7", and "Bin5" as illustrated in FIG. 7. The imaging control circuitry 33 then controls the acquisition circuitry 15 so as to perform preliminary imaging in accordance with the determined setting condition. The acquisition circuitry 15 thus switches a plurality of energy bins in which photons are counted in an energy bin discrimination process to energy bin "Bin6", energy bin "Bin7", and energy bin "Bin5" and executes an energy bin discrimination process. That is, the acquisition circuitry 15 creates, for each detection element, photon count data that is data indicating a count value of photons for each of energy bin "Bin6", energy bin "Bin7", and energy bin "Bin5" designated by the imaging control circuitry 33, and outputs the created photon count data to the imaging control circuitry 33 and the like. It is noted that such photon count data is an example of the second photon count data. The imaging control circuitry 33 then stores the imaging plan including the determined setting condition in association with the imaging timing into the storage circuitry 37.

Thresholds $\alpha 6$, $\alpha 7$, and $\alpha 5$ are set for energy bin "Bin6", energy bin "Bin7", and energy bin "Bin5", respectively. When the image generating circuitry 36 performs a material decomposition process on the photon count data created through the energy bin discrimination process using energy bin "Bin6", energy bin "Bin7", and energy bin "Bin5", three target substances "Gadolinium", "Bone", and "Platinum" are identified through the material decomposition process. Specifically, when the number of counted photons (the average of the numbers of photons in the region of interest in energy bin "Bin6") is greater than threshold $\alpha 6$ in energy bin "Bin6", the number of counted photons (the average of the numbers of photons in the region of interest in energy bin "Bin7") is greater than threshold $\alpha 7$ in energy bin "Bin7", and the number of counted photons (the average of the numbers of photons in the region of interest in energy bin "Bin5") is greater than threshold $\alpha 5$ in energy bin "Bin5", target substances "Gadolinium", "Bone", and "Platinum" can be identified through a material decomposition process. A plurality of energy bins "Bin6", "Bin7", and "Bin5" is therefore for identifying three target substances "Gadolinium", "Bone", and "Platinum". A plurality of energy bins "Bin6", "Bin7", and "Bin5" is an example of the second plurality of energy bins.

Case 7

A case where it is determined that the average "Count-Bin1" of the numbers of photons exceeds threshold $\alpha 1$, the average "Count-Bin2" of the numbers of photons exceeds threshold $\alpha 2$, and the average "Count-Bin3" of the numbers of photons is equal to or smaller than threshold $\alpha 3$ will be described (Case 7). In this case, similarly to Case 6, the imaging control circuitry 33 determines a setting condition for switching a plurality of energy bins in which photons are counted in an energy bin discrimination process to a plurality of energy bins "Bin6", "Bin7", and "Bin5" as previously illustrated in FIG. 7. The imaging control circuitry 33 then controls the acquisition circuitry 15 so as to perform preliminary imaging in accordance with the determined setting condition. The imaging control circuitry 33 then stores the imaging plan including the determined setting condition in association with the imaging timing into the storage circuitry 37.

Case 8

Figures 8, 9:
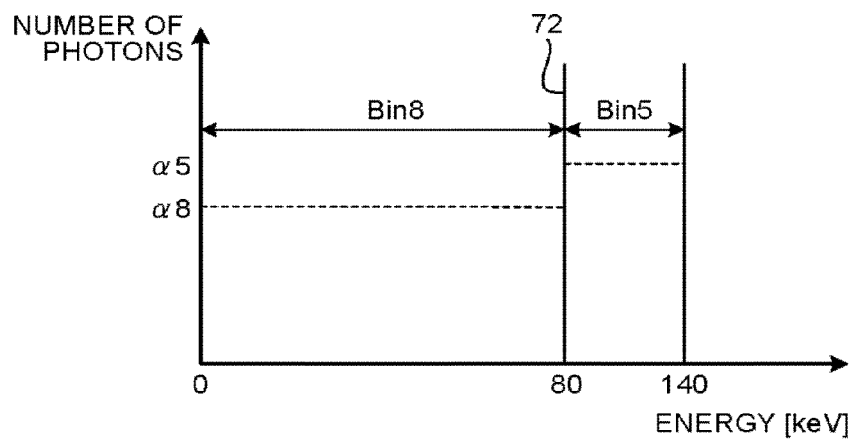
FIG. 8 is a diagram illustrating an example of a plurality of energy bins.
FIG. 9 is a diagram schematically illustrating an X-ray radiation condition determination method.

A case where it is determined that the average "Count-Bin1" of the numbers of photons exceeds threshold $\alpha 1$, the average "Count-Bin2" of the numbers of photons exceeds threshold $\alpha 2$, and the average "Count-Bin3" of the numbers of photons exceeds threshold $\alpha 3$ will be described (Case 8). In this case, photons are counted as many as three target substances "Iodine", "Gadolinium", and "Bone" can be identified through the material decomposition process executed by the image generating circuitry 36. In this case, the imaging control circuitry 33 therefore determines a setting condition for switching a plurality of energy bins in which photons are counted in an energy bin discrimination process to a plurality of energy bins "Bin8" and "Bin5" as illustrated in FIG. 8. The imaging control circuitry 33 then controls the acquisition circuitry 15 so as to perform preliminary imaging in accordance with the determined setting condition. The acquisition circuitry 15 thus switches a plurality of energy bins in which photons are counted in an energy bin discrimination process to energy bin "Bin8" and energy bin "Bin5" and executes an energy bin discrimination process. That is, the acquisition circuitry 15 creates, for each detection element, photon count data that is data indicating the count value of photons for each of energy bin "Bin8" and energy bin "Bin5" designated by the imaging control circuitry 33, and outputs the created photon count data to the imaging control circuitry 33 and the like. It is noted that such photon count data is an example of the second photon count data. The imaging control circuitry 33 then stores the imaging plan including the determined setting condition in association with the imaging timing into the storage circuitry 37.

Thresholds $\alpha 8$ and $\alpha 5$ are set for energy bin "Bin8" and energy bin "Bin5", respectively. When the image generating circuitry 36 performs a material decomposition process on the photon count data created through the energy bin discrimination process using energy bin "Bin8" and energy bin "Bin5", one target substance "Platinum" is identified through the material decomposition process. Specifically, when the number of counted photons (the average of the numbers of photons in the region of interest in energy bin "Bin8") is greater than threshold $\alpha 8$ in energy bin "Bin8", and the number of counted photons (the average of the count values of photons in the region of interest in energy bin "Bin5") is greater than threshold $\alpha 5$ in energy bin "Bin5", the target substance "Platinum" can be identified through a material decomposition process. A plurality of energy bins "Bin8" and "Bin5" is therefore for identifying one target substance "Platinum". A plurality of energy bins "Bin8" and "Bin5" is an example of the second plurality of energy bins.

In each of Case 5 to Case 8, the imaging control circuitry 33 performs the following process every time it receives photon count data output in a predetermined cycle from the acquisition circuitry 15 in which a plurality of energy bins in which photons are counted in an energy bin discrimination process have been switched. That is, the imaging control circuitry 33 determines whether the number of photons in each energy bin is increased to such an extent that all of the four target substances "Iodine", "Gadolinium", "Bone", and "Platinum" can be identified through a material decomposition process.

For example, in Case 5, photons necessary for identifying target substances in a material decomposition process have already been counted for "Bin2" and "Bin3". The imaging control circuitry 33 therefore determines whether the average "Count-Bin1" of the numbers of photons in the region of interest in energy bin "Bin1" exceeds threshold $\alpha 1$, the average "Count-Bin4" of the numbers of photons in the region of interest in energy bin "Bin4" exceeds threshold $\alpha 4$, and the average "Count-Bin5" of the numbers of photons in the region of interest in energy bin "Bin5" exceeds threshold $\alpha 5$. If it is determined that the average "Count-Bin1" of the numbers of photons in the region of interest in energy bin "Bin1" exceeds threshold $\alpha 1$, the average "Count-Bin4" of the numbers of photons in the region of interest in energy bin "Bin4" exceeds threshold $\alpha 4$, and the average "Count-Bin5" of the numbers of photons in the region of interest in energy bin "Bin5" exceeds threshold $\alpha 5$, the imaging control circuitry 33 determines that the number of photons in each energy bin is increased to such an extent that all of the four target substances "Iodine", "Gadolinium", "Bone", and "Platinum" can be identified. On the other hand, if it is determined that the average "Count-Bin1" of the numbers of photons in the region of interest in energy bin "Bin1" is equal to or smaller than threshold $\alpha 1$, the average "Count-Bin4" of the numbers of photons in the region of interest in energy bin "Bin4" is equal to or smaller than threshold $\alpha 4$, or the average "Count-Bin5" of the numbers of photons in the region of interest in energy bin "Bin5" is equal to or smaller than threshold $\alpha 5$, the imaging control circuitry 33 determines that the number of photons has not yet been increased to such an extent that all of the four target substances "Iodine", "Gadolinium", "Bone", and "Platinum" can be identified.

In Case 6, photons necessary for identifying target substances in a material decomposition process have already been counted for "Bin1" and "Bin3". The imaging control circuitry 33 therefore determines whether the average "Count-Bin6" of the numbers of photons in the region of interest in energy bin "Bin6" exceeds threshold $\alpha 6$, the average "Count-Bin7" of the numbers of photons in the region of interest in energy bin "Bin7" exceeds threshold $\alpha 7$, and the average "Count-Bin5" of the numbers of photons in the region of interest in energy bin "Bin5" exceeds threshold $\alpha 5$. If it is determined that the average "Count-Bin6" of the numbers of photons in the region of interest in energy bin "Bin6" exceeds threshold $\alpha 6$, the average "Count-Bin7" of the numbers of photons in the region of interest in energy bin "Bin7" exceeds threshold $\alpha 7$, and the average "Count-Bin5" of the numbers of photons in the region of interest in energy bin "Bin5" exceeds threshold $\alpha 5$, the imaging control circuitry 33 determines that the number of photons in each energy bin is increased to such an extent that all of the four target substances "Iodine", "Gadolinium", "Bone", and "Platinum" can be identified. On the other hand, if it is determined that the average "Count-Bin6" of the numbers of photons in the region of interest in energy bin "Bin6" is equal to or smaller than threshold $\alpha 6$, the average "Count-Bin7" of the numbers of photons in the region of interest in energy bin "Bin7" is equal to or smaller than threshold $\alpha 7$, or the average "Count-Bin5" of the numbers of photons in the region of interest in energy bin "Bin5" is equal to or smaller than threshold $\alpha 5$, the imaging control circuitry 33 determines that the number of photons has not yet been increased to such an extent that all of the four target substances "Iodine", "Gadolinium", "Bone", and "Platinum" can be identified.

In Case 7, photons necessary for identifying target substances in a material decomposition process have already been counted for "Bin1" and "Bin2". The imaging control circuitry 33 therefore determines whether the average "Count-Bin6" of the numbers of photons in the region of interest in energy bin "Bin6" exceeds threshold $\alpha 6$, the average "Count-Bin7" of the numbers of photons in the region of interest in energy bin "Bin7" exceeds threshold $\alpha 7$, and the average "Count-Bin5" of the numbers of photons in the region of interest in energy bin "Bin5" exceeds threshold $\alpha 5$. If it is determined that the average "Count-Bin6" of the numbers of photons in the region of interest in energy bin "Bin6" exceeds threshold $\alpha 6$, the average "Count-Bin7" of the numbers of photons in the region of interest in energy bin "Bin7" exceeds threshold $\alpha 7$, and the average "Count-Bin5" of the numbers of photons in the region of interest in energy bin "Bin5" exceeds threshold $\alpha 5$, the imaging control circuitry 33 determines that the number of photons in each energy bin is increased to such an extent that all of the four target substances "Iodine", "Gadolinium", "Bone", and "Platinum" can be identified. On the other hand, if it is determined that the average "Count-Bin6" of the numbers of photons in the region of interest in energy bin "Bin6" is equal to or smaller than threshold $\alpha 6$, the average "Count-Bin7" of the numbers of photons in the region of interest in energy bin "Bin7" is equal to or smaller than threshold $\alpha 7$, or the average "Count-Bin5" of the numbers of photons in the region of interest in energy bin "Bin5" is equal to or smaller than threshold $\alpha 5$, the imaging control circuitry 33 determines that the number of photons has not yet been increased to such an extent that all of the four target substances "Iodine", "Gadolinium", "Bone", and "Platinum" can be identified.

In Case 8, photons have already been counted as many as the target substances "Iodine", "Gadolinium", and "Bone" can be identified through a material decomposition process. The imaging control circuitry 33 therefore determines whether the average "Count-Bin8" of the numbers of photons in the region of interest in energy bin "Bin8" exceeds threshold $\alpha 8$ and the average "Count-Bin5" of the numbers of photons in the region of interest in energy bin "Bin5" exceeds threshold $\alpha 5$.

If it is determined that the average "Count-Bin8" of the numbers of photons in the region of interest in energy bin "Bin8" exceeds threshold $\alpha 8$ and the average "Count-Bin5" of the numbers of photons in the region of interest in energy bin "Bin5" exceeds threshold $\alpha 5$, the imaging control circuitry 33 determines that the number of photons in each energy bin is increased to such an extent that all of the four target substances "Iodine", "Gadolinium", "Bone", and "Platinum" can be identified. On the other hand, if it is determined that the average "Count-Bin8" of the numbers of photons in the region of interest in energy bin "Bin8" is equal to or smaller than threshold $\alpha 8$ or the average "Count-Bin5" of the numbers of photons in the region of interest in energy bin "Bin5" is equal to or smaller than threshold $\alpha 5$, the imaging control circuitry 33 determines that the number of photons has not yet been increased to such an extent that all of the four target substances "Iodine", "Gadolinium", "Bone", and "Platinum" can be identified.

If it is determined that the number of photons in each energy bin is increased to such an extent that all of the four target substances "Iodine", "Gadolinium", "Bone", and "Platinum" can be identified, the imaging control circuitry 33 controls the high voltage producing circuitry 11 so as to terminate emission of X-rays by the radiation device 12 in preliminary imaging, in order to terminate preliminary imaging.

An example of the setting condition determination method for determining a setting condition has been described above. Main imaging is performed in accordance with the imaging plan including the setting condition determined by the setting condition determination method as described above.

Here, we describe a case where switching to a plurality of energy bins "Bin6", "Bin7", and "Bin5" as illustrated in FIG. 7 is done in the foregoing Case 6 during imaging of one roentgenogram in main imaging. In this case, when it is determined that the number of photons in each energy bin is increased to such an extent that all of the four target substances "Iodine", "Gadolinium", "Bone", and "Platinum" can be identified, the imaging control circuitry 33 calculates the average "Count-Bin2" of the numbers of photons in the region of interest in "Bin2" as follows. That is, the imaging control circuitry 33 calculates the average "Count-Bin2" of the numbers of photons in the region of interest in "Bin2" by subtracting the average "Count-Bin1" of the numbers of photons in the region of interest in "Bin1" from the average "Count-Bin6" of the numbers of photons in the region of interest in "Bin6" to obtain the difference. The imaging control circuitry 33 then outputs the calculated average "Count-Bin2" to the image generating circuitry 36. Thus, all of the four target substances "Iodine", "Gadolinium", "Bone", and "Platinum" can be identified through a material decomposition process in the image generating circuitry 36.

A case where switching to a plurality of energy bins "Bin6", "Bin7", and "Bin5" as illustrated in FIG. 7 is done in the foregoing Case 7 during imaging of one roentgenogram in main imaging will be described. In this case, when it is determined that the number of photons in each energy bin is increased to such an extent that all of the four target substances "Iodine", "Gadolinium", "Bone", and "Platinum" can be identified, the imaging control circuitry 33 calculates the average "Count-Bin3" of the numbers of photons in the region of interest in "Bin3" as follows. That is, the imaging control circuitry 33 calculates the average "Count-Bin3" of the numbers of photons in the region of interest in "Bin3" by obtaining the sum of the average "Count-Bin7" of the numbers of photons in the region of interest in "Bin7" and the average "Count-Bin5" of the numbers of photons in the region of interest in "Bin5". The imaging control circuitry 33 then outputs the calculated average "Count-Bin3" to the image generating circuitry 36. Thus, all of the four target substances "Iodine", "Gadolinium", "Bone", and "Platinum" can be identified through a material decomposition process in the image generating circuitry 36.

As described above, the imaging control circuitry 33 determines a condition as follows in preliminary imaging. That is, the imaging control circuitry 33 determines a setting condition under which all of the target substances "Iodine", "Gadolinium", "Bone", and "Platinum" can be identified through the material decomposition process executed by the image generating circuitry 36. The image generating circuitry 36 thus can precisely identify all of the target substances "Iodine", "Gadolinium", "Bone", and "Platinum" through a material decomposition process using the photon count data obtained through main imaging based on the imaging plan including the determined setting condition. The X-ray diagnostic apparatus 1 according to the first embodiment thus can estimate many target substances with high precision.

An example of an X-ray radiation condition determination method for determining an X-ray radiation condition will now be described. The imaging control circuitry 33 determines an X-ray radiation condition in main imaging every time photon count data transmitted from the acquisition circuitry 15 in a predetermined cycle is received in preliminary imaging. The imaging control circuitry 33 according to the first embodiment determines, for example, an X-ray radiation condition concerning voltage and current of the X-ray tube 12a to be an X-ray radiation condition in main imaging. The imaging control circuitry 33 then controls the high voltage producing circuitry 11 and the drive circuitry 14 such that main imaging is performed in accordance with the determined X-ray radiation condition. That is, the imaging control circuitry 33 controls the radiation device 12 through the high voltage producing circuitry 11 and the drive circuitry 14 such that main imaging is performed in accordance with the imaging plan.

FIG. 9 is a diagram schematically illustrating the X-ray radiation condition determination method. Here, we describe a case where energy bin "Bin1", energy bin "Bin2", and energy bin "Bin3" are set, and the imaging control circuitry 33 determines an X-ray radiation condition based on the photon count data output from the acquisition circuitry 15 executing an energy bin discrimination process.

In the present embodiment, the imaging control circuitry 33 determines four kinds of X-ray radiation conditions, namely, an X-ray radiation condition for increasing tube current, an X-ray radiation condition for reducing tube current, an X-ray radiation condition for increasing tube voltage, and an X-ray radiation condition for reducing tube voltage.

First, tube current will be discussed. When tube current increases, the number of X-ray photons emitted from the X-ray tube 12a increases. When tube current increases, the number of photons increases generally at the same rate for all energy bins.

By contrast, when tube voltage increases, energy of X-ray photons emitted from the X-ray tube 12a increases. It follows that the peak of energy of the emitted X-rays shifts to the high energy side, so that the rate of increase of the count value of photons (count rate, the number of photons per unit time) in an energy bin with high energy increases, and conversely, the rate of increase of the count value of photons in an energy bin with low energy decreases.

Similarly, when tube voltage decreases, the energy of X-ray photons emitted from the X-ray tube 12a decreases, so that the rate of increase of the count value of photons in an energy bin with high energy decreases, and conversely, the rate of increase of the count value of photons in an energy bin with low energy increases.

Based on these phenomena, the imaging control circuitry 33 performs processing described below every time photon count data is received, in preliminary imaging. For example, first, the imaging control circuitry 33 determines whether the average "Count-Bin1" of the numbers of photons in the region of interest in energy bin "Bin1" indicated by the photon count data exceeds threshold $\alpha 1$, determines whether the average "Count-Bin2" of the numbers of photons in energy bin "Bin2" indicated by the photon count data exceeds threshold $\alpha 2$, and determines whether the average "Count-Bin3" of the numbers of photons in energy bin "Bin3" indicated by the photon count data exceeds threshold $\alpha 3$.

A case where the imaging control circuitry 33 determines that the average "Count-Bin1" of the numbers of photons exceeds threshold $\alpha 1$, the average "Count-Bin2" of the numbers of photons exceeds threshold $\alpha 2$, and the average "Count-Bin3" of the numbers of photons exceeds threshold $\alpha 3$, as illustrated in FIG. 9, will now be described. In this case, photons are counted as many as the three target substances "Iodine", "Gadolinium", and "Bone" can be identified through the material decomposition process executed by the image generating circuitry 36. In this case, the imaging control circuitry 33 therefore determines an X-ray radiation condition for keeping tube current and tube voltage as it is. For example, the imaging control circuitry 33 determines the present tube current and tube voltage as an X-ray radiation condition. The imaging control circuitry 33 then controls the high voltage producing circuitry 11 and the like so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons exceeds threshold $\alpha 1$, the average "Count-Bin2" of the numbers of photons exceeds threshold $\alpha 2$, and the average "Count-Bin3" of the numbers of photons is equal to or smaller than threshold $\alpha 3$, as illustrated in FIG. 9, will now be described. In this case, a sufficient number of photons are counted in the energy bins with low energy, whereas the number of photons is insufficient in the energy bin with high energy. The imaging control circuitry 33 therefore determines an X-ray radiation condition for increasing tube voltage. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons exceeds threshold $\alpha 1$, the average "Count-Bin2" of the numbers of photons is equal to or smaller than threshold $\alpha 2$, and the average "Count-Bin3" of the numbers of photons exceeds threshold $\alpha 3$, as illustrated in FIG. 9, will now be described. In this case, the imaging control circuitry 33 determines an X-ray radiation condition for increasing tube current, because increasing or reducing tube voltage may not be successful. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons exceeds threshold $\alpha 1$, the average "Count-Bin2" of the numbers of photons is equal to or smaller than threshold $\alpha 2$, and the average "Count-Bin3" of the numbers of photons is equal to or smaller than threshold $\alpha 3$, as illustrated in FIG. 9, will be described. In this case, a sufficient number of photons are counted in the energy bin with low energy, whereas the number of photons is insufficient in the energy bins with high energy. The imaging control circuitry 33 then determines an X-ray radiation condition for increasing tube voltage. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons is equal to or smaller than threshold $\alpha 1$, the average "Count-Bin2" of the numbers of photons exceeds threshold $\alpha 2$, and the average "Count-Bin3" of the numbers of photons exceeds threshold $\alpha 3$, as illustrated in FIG. 9, will be described. In this case, a sufficient number of photons are counted in the energy bins with high energy, whereas the number of photons is insufficient in the energy bin with low energy. The imaging control circuitry 33 then determines an X-ray radiation condition for reducing tube voltage. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons is equal to or smaller than threshold $\alpha 1$, the average "Count-Bin2" of the numbers of photons exceeds threshold $\alpha 2$, and the average "Count-Bin3" of the numbers of photons is equal to or smaller than threshold $\alpha 3$, as illustrated in FIG. 9, will be described. In this case, the imaging control circuitry 33 determines an X-ray radiation condition for increasing tube current, because increasing or reducing tube voltage may not be successful. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3, as illustrated in FIG. 9, will be described. In this case, a sufficient number of photons are counted in the energy bin with high energy, whereas the number of photons is insufficient in the energy bins with low energy. The imaging control circuitry 33 therefore determines an X-ray radiation condition for reducing tube voltage. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

A case where the imaging control circuitry 33 determines that the average "Count-Bin1" of the numbers of photons is equal to or smaller than threshold α1, the average "Count-Bin2" of the numbers of photons is equal to or smaller than threshold α2, and the average "Count-Bin3" of the numbers of photons is equal to or smaller than threshold α3, as illustrated in FIG. 9, will be described. In this case, it is necessary to increase tube current to increase the number of photons on the whole, because the number of photons is insufficient for all of the energy bins. The imaging control circuitry 33 then determines an X-ray radiation condition for increasing tube current. The imaging control circuitry 33 then controls the acquisition circuitry 15 so as to perform preliminary imaging in accordance with the determined X-ray radiation condition. The imaging control circuitry 33 then stores the imaging plan including the determined X-ray radiation condition in association with the imaging timing into the storage circuitry 37.

An example of the X-ray radiation condition determination method for determining a X-ray radiation condition has been described above. Main imaging is performed in accordance with the imaging plan including the X-ray radiation condition determined by the X-ray radiation condition determination method as described above. In such main imaging, the X-ray radiation condition is adaptively changed such that the count value is increased in an energy bin in which the number of photons is not sufficient. In the X-ray diagnostic apparatus 1 according to the first embodiment, therefore, the exposure dose can be reduced.

The X-ray diagnostic apparatus 1 according to the first embodiment has been described above. In the X-ray diagnostic apparatus 1 according to the first embodiment, many target substances can be estimated with high precision, and, in addition, the exposure dose can be reduced. The X-ray diagnostic apparatus 1 according to the first embodiment therefore has great convenience.

First Modification to First Embodiment

A first modification to the first embodiment will now be described. In the foregoing first embodiment, when it is determined that the average of the numbers of photons in some of the energy bins is equal to or smaller than a corresponding threshold, an X-ray radiation condition for "increasing tube current" or "changing tube voltage" is determined. In the first modification to the first embodiment, an X-ray radiation condition different from that in the first embodiment is determined in such a situation. FIG. 10 is a diagram schematically illustrating the X-ray radiation condition determination method according to the first modification to the first embodiment.

In FIG. 10, the same X-ray radiation condition is determined as the X-ray radiation condition determined in the case previously illustrated in FIG. 9, except for: the case where the average "Count-Bin1" of the numbers of photons exceeds threshold α1, the average "Count-Bin2" of the numbers of photons is equal to or smaller than threshold α2, and the average "Count-Bin3" of the numbers of photons is equal to or smaller than threshold α3; and the case where the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3. In the example in FIG. 9, in the case where 'the average "Count-Bin1" of the numbers of photons exceeds threshold α1, the average "Count-Bin2" of the numbers of photons is equal to or smaller than threshold α2, and the average "Count-Bin3" of the numbers of photons is equal to or smaller than threshold α3', an X-ray radiation condition for increasing tube voltage is determined. In the example in FIG. 9, in the case where 'the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3', an X-ray radiation condition for reducing tube voltage is determined.

On the other hand, in the first modification to the first embodiment, as illustrated in the example in FIG. 10, in both of the cases above, the imaging control circuitry 33 determines an X-ray radiation condition for increasing tube current. That is, the necessary count of photons is ensured in all of the energy bins by raising the count value of photons in all of the energy bins, rather than shifting the peak of X-ray energy.

Second Modification to First Embodiment

In the foregoing first embodiment, the imaging control circuitry 33 determines a setting condition in two levels, namely, whether the average of the numbers of photons in the region of interest in each energy bin is higher or lower than a corresponding threshold. However, the average of the numbers of photons in the region of interest in each energy bin may be classified into three or more levels, and a setting condition may be determined according to the result of the classification. Such an embodiment will be described as a second modification to the first embodiment.

FIG. 11 is a diagram for explaining an example of the setting condition determination process according to the second modification to the first embodiment. FIG. 11 is a diagram for explaining an example of the method of classifying the average of the numbers of photons in the region of interest in multiple levels, for each energy bin. Threshold C is additionally set for the average x of the numbers of photons in the region of interest, in each energy bin. Threshold C is a value smaller than thresholds α1 to α8 set in the energy bins as described in the first embodiment. It is noted that thresholds α1 to α8 may be collectively referred to as threshold α.

When the number of energy bins in which the average x of the numbers of photons in the region of interest is greater than threshold C and equal to or smaller than threshold α is one (when the count level is "L1"), the imaging control circuitry 33 performs the processing as described in the case that meets the conditions of the average x of the numbers of photons and threshold α, in Case 5 and Case 7.

When the number of energy bins in which the average x of the numbers of photons in the region of interest is equal to or smaller than threshold C is one (when the count level is "L2"), it can be assumed that almost no photons are counted in this energy bin. It is therefore preferable to increase the width of this energy bin to perform an energy bin discrimination process so that more photons are counted quickly. In Case 5 above, when the count level is "L2", the imaging control circuitry 33 controls the acquisition circuitry 15 so as to perform an energy bin discrimination process using a plurality of energy bins ("Bin1'", "Bin4", and "Bin5") obtained by increasing the width of energy bin "Bin1". Thus, more photons can be counted quickly. It is noted that "Bin1'" refers to an energy bin obtained by increasing the width of energy bin "Bin1".

In Case 7 above, when the count level is "L2", the imaging control circuitry 33 controls the acquisition circuitry 15 so as to perform an energy bin discrimination process using a plurality of energy bins ("Bin6", "Bin7'", and "Bin5") obtained by increasing the width of energy bin "Bin7". Thus, more photons can be counted quickly. It is noted that "Bin7'" refers to an energy bin obtained by increasing the width of energy bin "Bin7" to the low energy side.

In the second modification to the first embodiment as described above, even when the average x of the numbers of photons is equal to or smaller than threshold α, the width of the energy bin used when the acquisition circuitry 15 performs an energy bin discrimination process is appropriately changed depending on whether the average x is closer to threshold α or the average x is as small as threshold C or smaller. In the second modification to the first embodiment, therefore, many target substances can be estimated with high precision in a shorter time.

In addition, in the second modification to the first embodiment, when the average x of the numbers of photons is equal to or smaller than threshold C, the width of the energy bin used when the acquisition circuitry 15 performs an energy bin discrimination process can be changed to an energy bin having a width that enables identification of an unknown target substance. This case is effective when the target substance is unknown.

Third Modification to First Embodiment

In a third modification to the first embodiment, the setting condition and the X-ray radiation condition as well as the imaging plan at the start of preliminary imaging and main imaging may be preset for each of the retained radiation plans (drive plan, X-ray radiation plan). For example, the imaging control circuitry 33 determines an X-ray radiation condition using a parameter linked to a radiation plan for the subject P and determines an imaging plan including the determined X-ray radiation condition. Examples of the parameter linked to a radiation plan include a site of interest (substance), examination, subject body shape, and subject age. For example, the imaging control circuitry 33 determines an X-ray radiation condition using a parameter linked to a radiation plan according to a site to be imaged, a substance of interest, or an individual difference of the subject P.

As used herein, the "radiation plan" refers to a plan that defines an X-ray radiation condition including radiation time, intensity, energy, and range of X-rays to be emitted, and target substances, considering information including a target to be imaged, an individual difference of the subject, the kind of contrast medium used, and the age of the subject.

It is noted that an appropriate X-ray radiation condition varies depending on differences such as the target to be imaged. As a first example, an appropriate X-ray radiation condition (tube voltage, tube current) varies between imaging the chest and imaging the arm. This is because the absorption ratio of X-rays varies with the site to be imaged, and the thicknesses of the sites to be imaged are also different. As a second example, an appropriate X-ray radiation condition varies depending on the individual difference of the subject P. For example, the body thickness differs between a fat person and a thin person, and the energy and the intensity of X-rays to be emitted are different. As a third example, an appropriate X-ray radiation condition also varies depending on the kind of contrast medium used in contrast-enhanced imaging and the kind of substance of interest (target substance) in a material decomposition process.

The setting condition and the X-ray radiation condition as well as the imaging plan at the start are preset so as to be linked to a radiation plan, thereby enabling appropriate imaging depending on, for example, the target to be imaged.

Fourth Modification to First Embodiment

The average of the numbers of photons in the region of interest in each energy bin may be classified into three or more levels, and an X-ray radiation condition may be determined finely according to the result of the classification. Such an embodiment will be described as a fourth modification to the first embodiment.

FIG. 12 and FIG. 13 are diagrams for explaining an example of the X-ray radiation condition determination process according to the fourth modification to the first embodiment.

FIG. 12 illustrates an example of the method of classifying the average of the numbers of photons in the region of interest into multiple levels, for each energy bin. A first threshold "C1", a second threshold "C2", a third threshold "C3", and a fourth threshold "C4" are additionally set for the average x of the numbers of photons in the region of interest, in each energy bin. Thresholds C1 to C3 are values smaller than threshold α set in each energy bin described in the first embodiment. As for the magnitude relation among C1 to C4, C1<C2<C3<α<C4 holds. In the example illustrated in FIG. 12, when the average x of the numbers of photons in the region of interest is smaller than threshold C1, the imaging control circuitry 33 determines that the count level in the corresponding energy bin is "L1". When the average x of the numbers of photons in the region of interest is equal to or greater than threshold C1 and less than threshold C2, the imaging control circuitry 33 determines that the count level in the corresponding energy bin is "L2". When the average x of the numbers of photons in the region of interest is equal to or greater than threshold C2 and less than threshold C3, the imaging control circuitry 33 determines that the count level in the corresponding energy bin is "L3". When the average x of the numbers of photons in the region of interest exceeds threshold α and is equal to or greater than threshold C3 and less than threshold C4, the imaging control circuitry 33 determines that the count level in the corresponding energy bin is "H1". When the average x of the numbers of photons in the region of interest is equal to or greater than threshold C4, the imaging control circuitry 33 determines that the count level in the corresponding energy bin is "H2".

When the average x of the numbers of photons in the region of interest is equal to or smaller than threshold α for all of the energy bins, that is, when the count level is one of "L1", "L2", and "L3" in all of the energy bins, the imaging control circuitry 33 determines an X-ray radiation condition for increasing tube current.

In the fourth modification to the first embodiment, in this case, the imaging control circuitry 33 further changes the amount of tube current to be increased, depending on to what extent the number of photons is insufficient, as illustrated in FIG. 13.

In the case where the average x of the numbers of photons in the region of interest is equal to or smaller than threshold α for all of the energy bins, when the count level of one or more energy bins is "L1", it can be assumed that tube current is insufficient to a large degree, compared with the required amount. The imaging control circuitry 33 therefore determines an X-ray radiation condition for increasing tube current by 0.5 mA compared with the tube current at present. In the case where the average x of the numbers of photons in the region of interest is equal to or smaller than threshold α for all of the energy bins, when the count level is not "L1" in any of the energy bins and there are one or more "L2", tube current is insufficient to an intermediate degree, compared with the required amount. The imaging control circuitry 33 therefore determines an X-ray radiation condition for increasing tube current by 0.2 mA compared with the tube current at present. When the count level is "L3" in all of the energy bins, tube current is insufficient by a slight amount. The imaging control circuitry 33 therefore determines an X-ray radiation condition for increasing tube current by 0.1 mA compared with the tube current at present.

In this manner, fine control can be performed by classifying the number of photons of X-rays into multiple count levels for each energy bin, and the exposure dose to the subject P can be minimized.

Fifth Modification to First Embodiment

The storage circuitry 37 may store history information indicating the history of the imaging plan used in control in main imaging, and every time the imaging control circuitry 33 performs control so as to perform main imaging in accordance with the determined imaging plan, the imaging plan may be registered in the history information stored in the storage circuitry 37. The history of the imaging plan actually used in control in main imaging is thus registered in the history information. The user can refer to this history information to grasp the imaging plan actually used in control in main imaging. Such an embodiment will now be described as a fifth modification to the first embodiment.

Figures 14, 15:
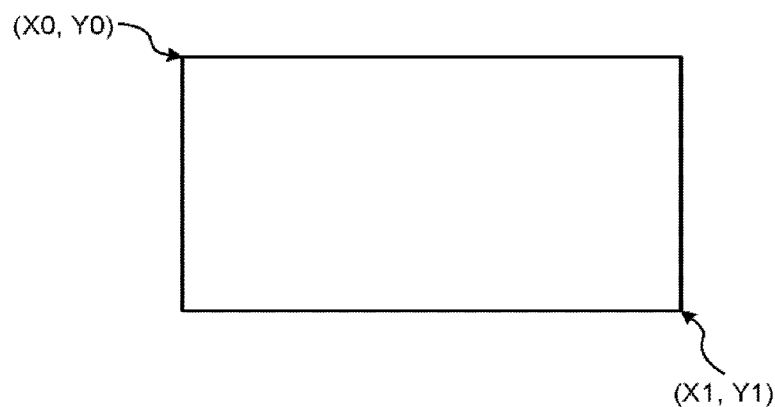
FIG. 14 is a diagram illustrating an example of the data structure of history information.
FIG. 15 is a diagram illustrating an example of a radiation range.

FIG. 14 is a diagram illustrating an example of the data structure of the history information. As illustrated in the example in FIG. 14, the history information has items "Time", "X-Ray kV", "X-Ray mA", "((X0,Y0,X1,Y2))", and "Type".

In the "Time" item, the time from the timing when main imaging is started to the timing when control is performed in accordance with the imaging plan in main imaging is registered. In the "X-Ray kV" item, the magnitude of tube voltage in units of "kV" is registered, with which the X-ray tube 12a is controlled at the time registered in the "Time" item of the same record. In the "X-Ray mA" item, the magnitude of tube current in units of "mA" is registered, with which the X-ray tube 12a is controlled at the time registered in the "Time" item of the same record. FIG. 15 is a diagram illustrating an example of the radiation range. In "(X0,Y0,X1,Y2)", as illustrated in FIG. 15, the position (X0,Y0) closest to the origin in the XY coordinates of the radiation range is registered, and the position (X1,Y1) furthest from the origin in the XY coordinates of the radiation range is also registered. In the "Type" item, the identifier of the radiation quality filter 12b used at the time registered in the "Time" item of the same record is registered. For example, the first record in the history information illustrated in the example in FIG. 14 indicates that at time "0", the imaging control circuitry 33 controls the X-ray tube 12a through the high voltage producing circuitry 11 such that the tube voltage reaches "90" kV and tube current flows at "100" mA, controls the X-ray beam limiting device 12c such that the position closest to the origin in the XY coordinates of the radiation range is (0,0) and the furthest position is (1024,1024), and performs control such that the radiation quality filter 12b indicated by the identifier "1" is moved to the front of the X-ray tube 12a. The X-ray output may be monitored using another detector capable of monitoring the output of the X-ray tube 12a (X-ray output).

Sixth Modification to First Embodiment

In the foregoing first embodiment, the imaging control circuitry 33 determines a setting condition and an X-ray radiation condition in preliminary imaging performed prior to main imaging and determines an imaging plan including the determined setting condition and X-ray radiation condition. The imaging control circuitry 33, however, may additionally update the imaging plan based on the photon count data output from the acquisition circuitry 15, during main imaging based on the imaging plan determined in preliminary imaging, and perform control such that main imaging is performed in accordance with the updated imaging plan.

For example, the imaging control circuitry 33 periodically determines a setting condition and an X-ray radiation condition, based on the photon count data output from the acquisition circuitry 15, during main imaging based on the imaging plan determined in preliminary imaging. The imaging control circuitry 33 then updates the setting condition and X-ray radiation condition determined in preliminary imaging with the setting condition and X-ray radiation condition determined during main imaging. The imaging control circuitry 33 then determines an imaging plan including the updated setting condition and X-ray radiation condition during main imaging and controls the radiation device 12 through the high voltage producing circuitry 11 and the drive circuitry 14 and also controls the acquisition circuitry 15 such that main imaging is performed in accordance with the determined imaging plan. Feedback control is thus performed, in which a setting condition and an X-ray radiation condition are determined based on the photon count data output by the acquisition circuitry 15 in real time (on time) during main imaging, and the high voltage producing circuitry 11, the drive circuitry 14, and the acquisition circuitry 15 are controlled such that main imaging is performed in accordance with the imaging plan including the determined setting condition and X-ray radiation condition. Accordingly, many target substances can be estimated with even higher precision and, in addition, the exposure dose can be further reduced. The X-ray diagnostic apparatus according to the sixth modification to the first embodiment therefore has even greater convenience.

Second Embodiment

In the foregoing first embodiment and modifications, the imaging control circuitry 33 compares the average x of the numbers of photons in the region of interest with threshold α for each energy bin and determines an imaging plan in accordance with the comparison result. The imaging control circuitry 33, however, may determine a setting condition in main imaging and an X-ray radiation condition in main imaging in accordance with the result of comparison of a noise component for each of a plurality of energy bins defined by the average x of the numbers of photons in the region of interest for each of the plurality of energy bins, with a corresponding predetermined threshold. Such an embodiment will now be described as a second embodiment.

First, an example of the method of calculating a noise component will be described. For example, the imaging control circuitry 33 calculates a noise component for each energy bin. A description will be given with a specific example. The imaging control circuitry 33 calculates, as a noise component, a standard deviation indicating a variation of the number of photons in the region of interest, from the number of photons of all the X-rays corresponding to all of the detection elements in the region of interest and the average x of the numbers of photons in the region of interest, for each energy bin, based on the photon count data output from the acquisition circuitry 15. Here, the larger a variation of the number of photons in the region of interest is, the larger the noise component is. Thus, the larger the standard deviation is, the larger the noise component is. Since photon count data is output from the acquisition circuitry 15 in a predetermined cycle, the imaging control circuitry 33 may further calculate a noise component based on a plurality of photon count data in the time axis direction. That is, the imaging control circuitry 33 may calculate a noise component, taking into consideration a variation of the average of the numbers of photons in the region of interest over time in the same detection element.

In the second embodiment, a threshold used for comparison with a noise component is defined for each energy bin. In the foregoing first embodiment and modifications, when the average x of the numbers of photons in the region of interest exceeds threshold α, the number of photons of X-rays necessary for generating one roentgenogram is sufficient in the corresponding energy bin. In generating a roentgenogram, a noise component is desired to be as small as possible. The imaging control circuitry 33 according to the second embodiment determines whether the noise component is equal to or smaller than a corresponding threshold, for each energy bin, and determines a setting condition in main imaging and an X-ray radiation condition in main imaging in accordance with the determination result. In the example described below, the imaging control circuitry 33 determines a setting condition in main imaging. The imaging control circuitry 33 can determine an X-ray radiation condition in main imaging by the same method.

FIG. 16 is a diagram schematically illustrating the setting condition determination method according to the second embodiment. In FIG. 16, when compared with the previous FIG. 5, "L" and "H" are reversed. This is because when the noise component is equal to or smaller than a corresponding threshold, the magnitude of noise component is thought to be permissible in generating a roentgenogram, in the corresponding energy bin.

Among Cases 9 to 16 in the example in FIG. 16, Case 9 will be described by way of example. That is, a case where the imaging control circuitry 33 determines that the noise component in energy bin "Bin1" exceeds a corresponding threshold, the noise component in energy bin "Bin2" exceeds a corresponding threshold, and the noise component in energy bin "Bin3" exceeds a corresponding threshold will be described. In this case, it can be assumed that none of the three target substances "Iodine", "Gadolinium", and "Bone" can be identified through the material decomposition process executed by the image generating circuitry 36, because the noise component is large in all of the energy bins. The imaging control circuitry 33 therefore determines a setting condition for allowing the acquisition circuitry 15 to keep a plurality of energy bins in which photons are counted, as it is, for example, a setting condition for keeping energy bin "Bin1", energy bin "Bin2", and energy bin "Bin3" at present, as illustrated in FIG. 16. For Cases 10 to 16, the imaging control circuitry 33 determines a setting condition illustrated in the example in FIG. 16, similarly.

Third Embodiment

In the foregoing first embodiment, the imaging control circuitry 33 determines a setting condition in main imaging and an X-ray radiation condition in main imaging, based on the photon count data output from the acquisition circuitry 15. The imaging control circuitry 33, however, may determine a setting condition in main imaging and an X-ray radiation condition in main imaging, based on image data of the subject P generated in the past by the X-ray diagnostic apparatus 1, any other X-ray diagnostic apparatus, an X-ray computed tomography (CT) apparatus, or a magnetic resonance imaging (MRI) apparatus. Such an embodiment will now be described as a third embodiment.

In the third embodiment, the image data of the subject P as described above is stored in the storage circuitry 37.

FIG. 17 is a flowchart illustrating the procedure of the imaging control process executed by the imaging control circuitry according to the third embodiment.

As illustrated in the example in FIG. 17, the imaging control circuitry 33 obtains image data of the subject P from the storage circuitry 37 (step S201). When image data of the subject P is retained in an external device, the imaging control circuitry 33 may obtain the image data of the subject P from the external device.

The imaging control circuitry 33 then determines a setting condition in main imaging and an X-ray radiation condition in main imaging, based on the obtained image data (step S202). For example, at step S202, the imaging control circuitry 33 estimates photon count data indicating the number of photons for each of a plurality of energy bins for each detection element, from the image data of the subject P, using the characteristics of a known target substance. The imaging control circuitry 33 then determines a setting condition in main imaging and an X-ray radiation condition in main imaging, based on the estimated photon count data, by the same method as in the foregoing first embodiment and modifications. At step S202, the imaging control circuitry 33 estimates an imaging timing supposing that the high voltage producing circuitry 11, the drive circuitry 14, and the acquisition circuitry 15 are controlled so as to perform preliminary imaging in accordance with the determined setting condition and X-ray radiation condition.

The imaging control circuitry 33 then determines an imaging plan including the determined setting condition and X-ray radiation condition (step S203). The imaging control circuitry 33 then stores the determined imaging plan in association with the estimated imaging timing into the storage circuitry 37 (step S204). The imaging control circuitry 33 then controls the high voltage producing circuitry 11, the drive circuitry 14, and the acquisition circuitry 15 so as to perform main imaging in accordance with the determined imaging plan (step S205). The imaging control process then ends.

The third embodiment has been described above. According to the third embodiment, many target substances can be estimated with high precision and, in addition, the exposure dose can be reduced, as in the first embodiment. The X-ray diagnostic apparatus according to the third embodiment therefore has great convenience.

Fourth Embodiment

A fourth embodiment will now be described. In the foregoing first embodiment, the imaging control circuitry 33 determines a setting condition in main imaging and an X-ray radiation condition in main imaging, based on the average x of the numbers of photons in the region of interest. In the fourth embodiment described below, the imaging control circuitry 33 determines a setting condition in main imaging and an X-ray radiation condition in main imaging, based on the quantity (information) other than the average x of the numbers of photons in the region of interest.

In the fourth embodiment, the imaging control circuitry 33 determines a setting condition in main imaging and an X-ray radiation condition in main imaging, based on the count value per unit time for each of a plurality of energy bins (for example, the average of the count values of photons per unit time for each energy bin of a plurality of detection elements in the region of interest (hereinafter referred to as the average per unit time of the numbers of photons in the region of interest)).

One of the reasons why the average per unit time of the numbers of photons in the region of interest is used rather than using the average of the numbers of photons in the region of interest is to take measures against the aforementioned pulse pile-up.

The probability of occurrence of pulse pile-up increases as the number of photons of X-rays incident per unit time increases. For example, the imaging control circuitry 33 determines an X-ray radiation condition using the average per unit time of the numbers of photons in the region of interest in the same manner as in the first embodiment and, when the average per unit time of the numbers of photons in the region of interest exceeds a predetermined threshold, performs control to prevent further increase of tube current, thereby taking measures against pulse pile-up.

The imaging control circuitry 33 can use the average per unit time of the numbers of photons in the region of interest as a criterion for judging whether to determine an X-ray radiation condition for changing the value of tube current or to determine an X-ray radiation condition for changing the value of tube voltage. For example, the imaging control circuitry 33 determines an X-ray radiation condition for increasing tube current when the average per unit time of the numbers of photons in the region of interest is equal to or smaller than a predetermined threshold. The imaging control circuitry 33 determines an X-ray radiation condition for changing tube voltage when the average per unit time of the numbers of photons in the region of interest exceeds a predetermined threshold, because further increase of tube current may cause pulse pile-up.

As described above, in the fourth embodiment, the exposure dose can be reduced and, in addition, the probability of occurrence of pulse pile-up can be reduced.

Fifth Embodiment

A fifth embodiment will now be described. In the foregoing first to fourth embodiments, the imaging control circuitry 33 determines an X-ray radiation condition concerning voltage and current of the X-ray tube 12a, such as tube voltage and tube current. In the fifth embodiment, the imaging control circuitry 33 determines an X-ray radiation condition concerning control on the radiation quality filter 12b of the X-ray tube 12a and determines an imaging plan including the X-ray condition concerning control on the radiation quality filter 12b.

The radiation quality filter 12b is a filter used for cutting off X-rays of particular energy as described above and is made of, for example, aluminum. The radiation quality filter 12b is typically used for cutting off soft X-rays (X-rays having long wavelengths and low energy). The imaging control circuitry 33 can reduce the exposure dose to the subject P also by controlling whether to use the radiation quality filter 12b, based on the count value of photons for each energy bin.

FIG. 18 and FIG. 19 are diagrams for explaining an example of the imaging control process according to the fifth embodiment. It is assumed that the radiation quality filter 12b selectively cuts off X-rays included in the range of energy bin "Bin1". The imaging control circuitry 33 according to the fifth embodiment determines whether the average of the numbers of photons in the region of interest exceeds a corresponding threshold, for energy bin "Bin2" and energy bin "Bin3", in the same manner as in the first embodiment. As for energy bin "Bin1", the determination conditions illustrated in FIG. 18 are used to determine the count level.

FIG. 18 is a diagram for explaining to which count level the imaging control circuitry 33 allocates the average of the numbers of photons in the region of interest, for energy bin "Bin1 corresponding to the radiation quality filter 12b, in the fifth embodiment. Here, the average of the numbers of photons in the region of interest in energy bin "Bin1" is "x", the first threshold is "C1", and the second threshold is "C2". As for the magnitude relation between C1 and C2, $C1<\alpha1<C2$ holds. The imaging control circuitry 33 determines that the count level of energy bin "Bin1" is "L" when the average x of the numbers of photons in the region of interest in energy bin "Bin1" is smaller than the first threshold C1. The imaging control circuitry 33 determines that the count level of energy bin "Bin1" is "H1" when the average x of the numbers of photons in the region of interest in energy bin "Bin1" is equal to or greater than the first threshold C1 and less than the second threshold C2. The imaging control circuitry 33 determines that the count level of energy bin "Bin1" is "H2" when the average x of the numbers of photons in the region of interest in energy bin "Bin1" is equal to or greater than the second threshold C2.

FIG. 19 is a diagram for explaining an example of the radiation quality filter control in the fifth embodiment. When the count level of energy bin "Bin1" is "H1", the average of the numbers of photons in the region of interest in energy bin "Bin2" exceeds threshold $\alpha2$, and the average of the numbers of photons in the region of interest in energy bin "Bin3" is equal to or smaller than threshold $\alpha3$, the imaging control circuitry 33 determines an X-ray radiation condition for increasing tube voltage. In main imaging based on the X-ray radiation condition for increasing tube voltage, tube voltage is shifted to the high voltage side, and energy of X-rays is shifted to the high energy side. As a result of shifting of tube voltage to the high voltage side, energy of X-rays is shifted to the high energy side on the whole. It is therefore thought that the average of the numbers of photons in the region of interest in energy bin "Bin1" will hereafter not increase so much.

Next, when the count level of energy bin "Bin1" is "H2", the average of the numbers of photons in the region of interest in energy bin "Bin2" exceeds threshold $\alpha2$, and the average of the numbers of photons in the region of interest in energy bin "Bin3" is equal to or smaller than threshold $\alpha3$, the imaging control circuitry 33 determines an X-ray radiation condition for increasing tube voltage, in the same manner as when the count level of energy bin "Bin1" is "H1". In main imaging based on the X-ray radiation condition for increasing tube voltage, even considering that an increase of the average of the numbers of photons in the region of interest in energy bin "Bin1" is suppressed, a sufficient number of photons have been obtained for energy bin "Bin1", given that the count level of energy bin "Bin1" is "H2". Accordingly, for energy bin "Bin1", emission of X-rays is no longer necessary. The imaging control circuitry 33 then determines an X-ray radiation condition for increasing tube voltage and also moving the radiation quality filter 12b to the front of the X-ray tube 12a for selectively cutting off X-rays having energy values included in the range of energy bin "Bin1". In main imaging based on such an X-ray radiation condition, the radiation quality filter 12b can suppress emission of X-rays having energy values within the range of energy bin "Bin1" to the subject P.

As described above, in the fifth embodiment, for example, tube voltage and tube current are controlled to changed based on the number of photons and, in addition, whether to use the radiation quality filter 12b is controlled, whereby unnecessary emission of X-rays having energy values within energy bin "Bin1" to the subject P can be suppressed. That is, unnecessary exposure can be suppressed. It is noted that control for changing tube voltage and tube current and controlling whether to use the radiation quality filter 12b may be based on the number of photons per unit time rather than the number of photons.

Sixth Embodiment

In the foregoing first to fifth embodiments, the imaging control circuitry 33 determines an imaging plan, based on the average of the numbers of photons for each energy bin in one region of interest or the average of the numbers of photons per unit time. In a sixth embodiment described below, a plurality of regions of interest are present. In the sixth embodiment, the imaging control circuitry 33 determines a setting condition in main imaging and an X-ray radiation condition in main imaging, based on the average of the numbers of photons for each of a plurality of energy bins for each of a plurality of regions of interest.

In the sixth embodiment, the imaging control circuitry 33 determines not only an X-ray radiation condition concerning tube voltage and tube current of the X-ray tube 12a and the radiation quality filter 12b but also an X-ray radiation condition concerning the X-ray beam limiting device 12c or exposure adjustment control. As used herein, the "X-ray radiation condition concerning the X-ray beam limiting device 12c" is, for example, an X-ray radiation condition for controlling the spatial range of radiation of X-rays emitted from the X-ray tube 12a by the X-ray beam limiting device 12c. Controlling the spatial range of radiation of X-rays enables control of the amount of X-rays applied to the subject P. The "X-ray radiation condition concerning exposure adjustment control" similarly refers to an X-ray radiation condition for controlling the amount of X-rays applied to the subject P and typically focuses on controlling the amount of X-rays applied by controlling the time in which X-rays are emitted. As an example, exposure adjustment control refers to controlling the radiation device 12 so as to emit X-rays for a preset radiation time. As another example, exposure adjustment control refers to controlling the radiation device 12 based on an electrical signal indicating the incident X-ray dose obtained by a detector (not illustrated) for exposure adjustment so as to stop emission of X-rays when the incident X-ray dose indicated by the electrical signal reaches a predetermined value.

FIG. 20 is a diagram for explaining an example of the imaging control process according to the sixth embodiment. In the example in FIG. 20, the imaging control circuitry 33 determines an X-ray radiation condition concerning the X-ray beam limiting device 12c. In the sixth embodiment, two regions of interest, namely, Region 1 and Region 2, are set, and the X-ray beam limiting device 12c cuts off X-rays applied to Region 2 to control the amount of X-rays applied to Region 2. The imaging control circuitry 33 determines an X-ray radiation condition based on the average of the numbers of photons for each of a plurality of energy bins in Region 1 and the average of the numbers of photons for each of a plurality of energy bins in Region 2.

First, we describe a case where the average of the numbers of photons in Region 1 exceeds threshold $\alpha 1$ in energy bin "Bin1", the average of the numbers of photons in Region 2 exceeds threshold $\alpha 1$ in energy bin "Bin1", the average of the numbers of photons in Region 1 exceeds threshold $\alpha 2$ in energy "Bin2", the average of the numbers of photons in Region 2 exceeds threshold $\alpha 2$ in energy bin "Bin2", the average of the numbers of photons in Region 1 is equal to or smaller than threshold $\alpha 3$ in energy "Bin3", and the average of the numbers of photons in Region 2 is equal to or smaller than threshold $\alpha 3$ in energy bin "Bin3". In this case, as illustrated in the upper row in FIG. 20, the imaging control circuitry 33 determines an X-ray radiation condition for increasing tube voltage. Next, when the relation between the average of the numbers of photons in each energy bin and the threshold for each of Region 1 and Region 2 as illustrated in the upper row in FIG. 20 changes to the relation between the average of the numbers of photons in each energy bin and the threshold for each of Region 1 and Region 2 as illustrated in the lower row in FIG. 20, that is, when the average of the numbers of photons in all of the energy bins exceeds the threshold as for Region 2, further X-ray radiation is no longer necessary for Region 2. The imaging control circuitry 33 therefore determines an X-ray radiation condition for increasing tube voltage and cutting off X-rays applied to Region 2 by the X-ray beam limiting device 12c, as an X-ray radiation condition in main imaging.

In this manner, the X-ray diagnostic apparatus according to the sixth embodiment determines an X-ray radiation condition concerning the X-ray beam limiting device 12c, thereby effectively reducing the exposure dose. The imaging control circuitry 33 may determine an X-ray radiation condition concerning the X-ray beam limiting device 12c in main imaging, based on the sum of respective count values of a plurality of energy bins in each of a plurality of regions of interest. The imaging control circuitry 33 may determine an X-ray radiation condition concerning the X-ray beam limiting device 12c in main imaging, based on the average per unit time of the numbers of photons in the region of interest.

Seventh Embodiment

A seventh embodiment will now be described. In the seventh embodiment, the imaging control circuitry 33 determines two or more X-ray radiation conditions and determines an imaging plan including the determined two or more X-ray radiation conditions.

FIG. 21 is a diagram for explaining an example of the imaging control process according to the seventh embodiment. As illustrated by the example in FIG. 21, the X-ray radiation conditions are the same as the X-ray radiation conditions determined in the previous cases illustrated in FIG. 9 and FIG. 10, except for: the case where the average "Count-Bin1" of the numbers of photons exceeds threshold α1, the average "Count-Bin2" of the numbers of photons is equal to or smaller than threshold α2, and the average "Count-Bin3" of the numbers of photons is equal to or smaller than threshold α3; and the case where the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3. In the case where 'the average "Count-Bin1" of the numbers of photons exceeds threshold α1, the average "Count-Bin2" of the numbers of photons is equal to or smaller than threshold α2, and the average "Count-Bin3" of the numbers of photons is equal to or smaller than threshold α3', an X-ray radiation condition for increasing tube voltage is determined in the example in FIG. 9, and an X-ray radiation condition for increasing tube current is determined in the example in FIG. 10. In the case where 'the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3', an X-ray radiation condition for reducing tube voltage is determined in the example in FIG. 9, and an X-ray radiation condition for increasing tube current is determined in the example in FIG. 10.

On the other hand, the imaging control circuitry 33 according to the seventh embodiment determines an X-ray radiation condition for increasing tube voltage and increasing tube current, as an X-ray radiation condition in main imaging, as illustrated in the example in FIG. 21, in the case where 'the average "Count-Bin1" of the numbers of photons exceeds threshold α1, the average "Count-Bin2" of the numbers of photons is equal to or smaller than threshold α2, and the average "Count-Bin3" of the numbers of photons is equal to or smaller than threshold α3'.

The imaging control circuitry 33 according to the seventh embodiment determines an X-ray radiation condition for reducing tube voltage and also increasing tube current, as an X-ray radiation condition in main imaging, as illustrated in the example in FIG. 21, in the case where 'the average "Count-Bin1" of the numbers of photons is equal to or smaller than threshold α1, the average "Count-Bin2" of the numbers of photons is equal to or smaller than threshold α2, and the average "Count-Bin3" of the numbers of photons exceeds threshold α3'.

In the seventh embodiment, the imaging control circuitry 33 determines two or more X-ray radiation conditions and determines an imaging plan including the determined two or more X-ray radiation conditions, thereby precisely controlling X-ray radiation conditions in main imaging based on the determined imaging plan. In the seventh embodiment, the imaging control circuitry 33 registers information indicating the respective positions of Region 1 and Region 2 in the history information indicating history of X-ray radiation conditions.

First Modification to Seventh Embodiment

In a first modification to the seventh embodiment, when the values of tube voltage and tube current are simultaneously controlled, the imaging control circuitry 33 makes a calculation as to what values are defined for tube voltage and tube current, by a predetermined method. FIG. 22 is a diagram for explaining the first modification to the seventh embodiment. The example in FIG. 22 illustrates an example of the method of calculating the values of tube voltage and tube current.

As illustrated in FIG. 22, the imaging control circuitry 33 determines an X-ray radiation condition for changing tube voltage by a tube voltage change amount $\delta V$ and also changing tube current by a tube current change amount $\delta I$. The X-ray count f is defined as f(E,I) as a function of tube current and energy of X-rays, where I is tube current and E is energy of X-rays.

The exposure dose P of X-rays is uniquely defined if the tube voltage change amount $\delta V$ and the tube current change amount $\delta I$ are defined. The exposure dose P therefore is a function of $\delta V$ and $\delta I$. Under the constraint condition that a predetermined condition necessary for main imaging should be satisfied, $P(\delta V, \delta I)$ is minimized to obtain an objective function. An example of the sufficient condition for "satisfying a predetermined condition necessary for main imaging" may be, for example, a condition that "when tube voltage and tube current are changed, the predicted average $X_i$ of the number of photons in the i-th energy bin in increasing order of energy values should exceed threshold $Th_i$ set for the i-th energy bin".

The predicted average $X_i$ is calculated by the equation "$X_i = C_i \times (1 + A_i \times \delta V + B_i \times \delta I)$", where $C_i$ is the average of the numbers of photons in the i-th energy bin in increasing order of energy value, and $A_i$ and $B_i$ are coefficients.

Here, $C_i$ is the average at present, and coefficients $A_i$ and $B_i$ can be easily obtained from the X-ray count f as a function of tube current I and energy E of X-rays, noting that "$X_i = f(E + \delta V, I + \delta I) \approx f(E,I) + \delta V \times \partial f/\partial E + \delta I \times \partial f/\partial I$".

Since both of the constraint condition and the objective function are uniquely defined as a function of $\delta V$ and $\delta I$, the imaging control circuitry 33 can calculate the appropriate tube voltage change amount $\delta V$ and tube current change amount $\delta I$ using a predetermined method such as linear programming, the least-squares method, the method of Lagrange multiplier, or the calculus of variations. As a result, the imaging control circuitry 33 can determine an X-ray radiation condition for changing tube voltage by the tube voltage change amount $\delta V$ and also changing tube current by the tube current change amount $\delta I$. In the first modification to the seventh embodiment, the imaging control circuitry 33 can calculate the amounts of tube voltage and tube current to be changed in main imaging, with high precision.

Second Modification to Seventh Embodiment

In a second modification to the seventh embodiment, the imaging control circuitry 33 determines what setting condition and X-ray radiation condition are to be determined, using different kinds of information. That is, in the second modification to the seventh embodiment, the imaging control circuitry 33 determines what setting condition and X-ray radiation condition are to be determined, based on two or more kinds of information, among the average of the numbers of photons for each energy bin in the region of interest, the average of the numbers of photons per unit time for each energy bin in the region of interest, the sum of the averages of the numbers of photons for all the energy bins in the region of interest, and the sum of the averages of the numbers of photons per unit time for all the energy bins in the region of interest.

FIG. 23 is a diagram for explaining the second modification to the seventh embodiment. FIG. 23 illustrates an example of the X-ray radiation condition determination method executed by the imaging control circuitry 33 in the second modification to the seventh embodiment. In the second modification to the seventh embodiment, the imaging control circuitry 33 determines an X-ray radiation condition, for example, using both of the average of the numbers of photons for each energy bin in the region of interest and the average of the numbers of photons per unit time for each energy bin in the region of interest.

Now, we will describe a case where the average of the numbers of photons in energy bin "Bin1" in the region of interest, the average of the numbers of photons per unit time in energy bin "Bin1" in the region of interest, the average of the numbers of photons in energy bin "Bin2" in the region of interest, and the average of the numbers of photons per unit time in energy bin "Bin2" in the region of interest are each equal to or smaller than the corresponding threshold.

In this case, as illustrated in the example in FIG. 23, when the average of the numbers of photons (count) in energy bin "Bin3" in the region of interest is equal to or smaller than the corresponding threshold and the average of the numbers of photons per unit time (count rate) in energy bin "Bin3" in the region of interest is also equal to or smaller than the corresponding threshold, the imaging control circuitry 33 determines an X-ray radiation condition for increasing tube current.

As illustrated in the example in FIG. 23, when the average of the numbers of photons (count) in energy bin "Bin3" in the region of interest exceeds the corresponding threshold and the average of the numbers of photons per unit time (count rate) in energy bin "Bin3" in the region of interest also exceeds the corresponding threshold, the imaging control circuitry 33 performs the processing as follows. That is, the imaging control circuitry 33 determines an X-ray radiation condition for reducing tube voltage.

A case where the average of the numbers of photons (count) in energy bin "Bin3" in the region of interest is equal to or smaller than the corresponding threshold and the average of the numbers of photons per unit time (count rate) in energy bin "Bin3" in the region of interest exceeds the corresponding threshold, as illustrated in the example in FIG. 23, will be described. In this case, the count rate exceeds the threshold, and if tube current is further increased, pulse pile-up may possibly occur. The imaging control circuitry 33 therefore determines an X-ray radiation condition for reducing tube voltage, rather than an X-ray radiation condition for increasing tube current.

A case where the average of the numbers of photons (count) in energy bin "Bin3" in the region of interest exceeds the corresponding threshold and the average of the numbers of photons per unit time (count rate) in energy bin "Bin3" in the region of interest is equal to or smaller than the corresponding threshold, as illustrated in the example in FIG. 23, will be described. In this case, given that the count rate is equal to or smaller than the threshold, the possibility that increasing tube current causes pulse pile-up is low. The imaging control circuitry 33 therefore determines an X-ray radiation condition for reducing tube voltage and also increasing tube current.

In this manner, the X-ray diagnostic apparatus according to the second modification to the seventh embodiment uses different kinds of information as criteria for determining an X-ray radiation condition. In the second modification to the seventh embodiment, an X-ray radiation condition thus can be determined more precisely. In the second modification to the seventh embodiment, when a plurality of regions of interest are set, an X-ray radiation condition may be determined as described above for each region of interest. In the second modification to the seventh embodiment, when a plurality of regions of interest are set, the imaging control circuitry 33 may determine an X-ray radiation condition in each region of interest, based on the sum of the averages of the numbers of photons for all the energy bins in each region of interest and the sum of the averages of the numbers of photons per unit time for all the energy bins in each region of interest.

Eighth Embodiment

In the foregoing first to seventh embodiments and modifications, the control amount of tube voltage, the control amount of tube current, and the like are fixed values. In an eighth embodiment, a variety of control amounts such as the control amount of tube voltage and the control amount of tube current are changed. In the X-ray diagnostic apparatus according to the eighth embodiment, the imaging control circuitry 33 changes the control amount of tube voltage, the control amount of tube current, and the like in accordance with photon count data. FIG. 24 is a diagram for explaining an example of the imaging control process according to the eighth embodiment.

Now, we describe a case where three energy bins, namely, energy bin "Bin1", energy bin "Bin2", and energy bin "Bin3" are set in the acquisition circuitry 15. Here, it is assumed that the average x of the numbers of photons in the region of interest is equal to or smaller than threshold α, for all of the energy bins. That is, the count level is any one of "L1", "L2", and "L3" in all of the energy bins. In the eighth embodiment, the imaging control circuitry 33 determines which of "L1", "L2", and "L3" the count level for each energy bin is, in the same manner as in the foregoing fourth modification to the first embodiment. The imaging control circuitry 33 then determines the control amount of tube current in accordance with the count level of the energy bin.

Here, the imaging control circuitry 33 includes the control amount at present in an X-ray radiation condition for increasing tube current. As an initial value of the control amount at present, for example, the amount "0 mA" is given. Upon determining an X-ray radiation condition for increasing tube current, the imaging control circuitry 33 updates the control amount at present. For example, when the control amount at present is 0 mA and the count levels of the three energy bins include one or more "L1", the imaging control circuitry 33 calculates "x+0.5" as the control amount after change, where "x" is the control amount at present. That is, when the control amount at present is "0 mA", the control amount after change is "0+0.5=0.5 mA". Accordingly, when the count levels of the three energy bins include one or more "L1", the imaging control circuitry 33 determines such an X-ray radiation condition that increases tube current by "0.5 mA" from the tube current at present. In doing so, the imaging control circuitry 33 includes the control amount after change as the control amount at present in the X-ray radiation condition.

For example, it is assumed that when the control amount at present is 0.5 mA, the imaging control circuitry 33 obtains new photon count data from the acquisition circuitry 15. We describe a case where, in this situation, the count levels of the three energy bins include no "L1" and one or more "L2" due to the increase of tube current. In this case, the imaging control circuitry 33 calculates "x+0.2" as the control amount after change, where "x" is the control amount at present. Here, given that the control amount at present is "0.5 mA", the control amount after change is "0.5+0.2=0.7 mA". The imaging control circuitry 33 then determines such an X-ray radiation condition that increases tube current by 0.7 mA from the tube current at present, and also includes "0.7 mA" as the control amount at present in the X-ray radiation condition.

For example, it is assumed that when the control amount at present is 0.5 mA, the imaging control circuitry 33 obtains new count data from the acquisition circuitry 15. We describe a case where, in this situation, the count levels of the three energy bins are all "L3" due to the increase of tube current. In this case, the imaging control circuitry 33 calculates "x+0.1" as the control amount after change, where "x" is the control amount at present. Here, given that the control amount at present is "0.5 mA", the control amount after change is "0.5+0.1=0.6 mA". The imaging control circuitry 33 therefore determines such an X-ray radiation condition that increases tube current by 0.6 mA from the tube current at present, and also includes "0.6 mA" as the control amount at present in the X-ray radiation condition.

Next, the operation in a case where the imaging control circuitry 33 determines an X-ray radiation condition other than the X-ray radiation condition for increasing tube current will be described. In this case, the imaging control circuitry 33 resets the control amount at present included in the X-ray radiation condition for increasing tube current, to an initial value. For example, when the control amount at present is "0.6 mA", if the imaging control circuitry 33 determines an X-ray radiation condition for reducing tube current or an X-ray radiation condition for increasing tube voltage, then the control amount at present included in the X-ray radiation condition for increasing tube current is "0 mA". At the same time, the imaging control circuitry 33 updates the control amount at present included in the X-ray radiation condition for reducing tube current or the X-ray radiation condition for increasing tube voltage, with a predetermined value.

The imaging control circuitry 33 can dynamically change the control amount at present included in the X-ray radiation condition in accordance with photon count data, thereby quickly bringing any X-ray radiation condition at present closer to the optimum X-ray radiation condition. For example, a case where the voltage value at present is 20 keV, and the optimum voltage value is 20.1 keV or 50 keV will be described. When the control amount is 0.1 keV, 20.1 keV can be reached by determining an X-ray radiation condition once, whereas reaching 50 keV requires determining an X-ray radiation condition (50−20)/0.1=300 times. On the other hand, when the control amount is 10 keV, 50 keV can be reached by determining an X-ray radiation condition three times, whereas the control amount each time is so large that the voltage goes beyond 20.1 keV and fails to reach 20.1 keV.

On the other hand, when the imaging control circuitry 33 dynamically changes the control amount in accordance with photon count data, for example, when 0.1 keV is added to the control amount at present to obtain the control amount after change, the control amount increases at an accelerated pace, so that 20.1 keV can be reached by determining an X-ray radiation condition once and 50 keV can be reached by determining an X-ray radiation condition 24 times. That is, in a first modification to the eighth embodiment, the control amount in the X-ray radiation condition is dynamically changed to bring the X-ray radiation condition closer to the optimum one quickly, thereby further reducing the exposure dose.

Second Modification to Eighth Embodiment

In a second modification to the eighth embodiment, the imaging control circuitry 33 may dynamically change a parameter used in determining a setting condition and an X-ray radiation condition, in place of the control amount. In the second modification to the eighth embodiment, the imaging control circuitry 33 changes a parameter based on photon count data to change the operation in determining an imaging plan.

Examples of the parameter changed dynamically include the time interval at which an imaging plan is determined. For example, in the second modification to the eighth embodiment, the time interval at which an imaging plan is determined is "one second", and a threshold is set for the average of the numbers of photons per unit time in each of a plurality of energy bins in the region of interest. In the second modification to the eighth embodiment, when the average of the numbers of photons per unit time in at least one energy bin exceeds a threshold, the imaging control circuitry 33 determines that the number of photons rapidly increases, and then changes the time interval to "0.5 seconds" and determines an imaging plan.

In the second modification to the eighth embodiment, for example, the time interval at which an imaging plan is determined is dynamically reduced in accordance with the average of the numbers of photons per unit time in an energy bin in the region of interest. The exposure dose thus can be reduced reliably.

Ninth Embodiment and Tenth Embodiment

Figure 25:
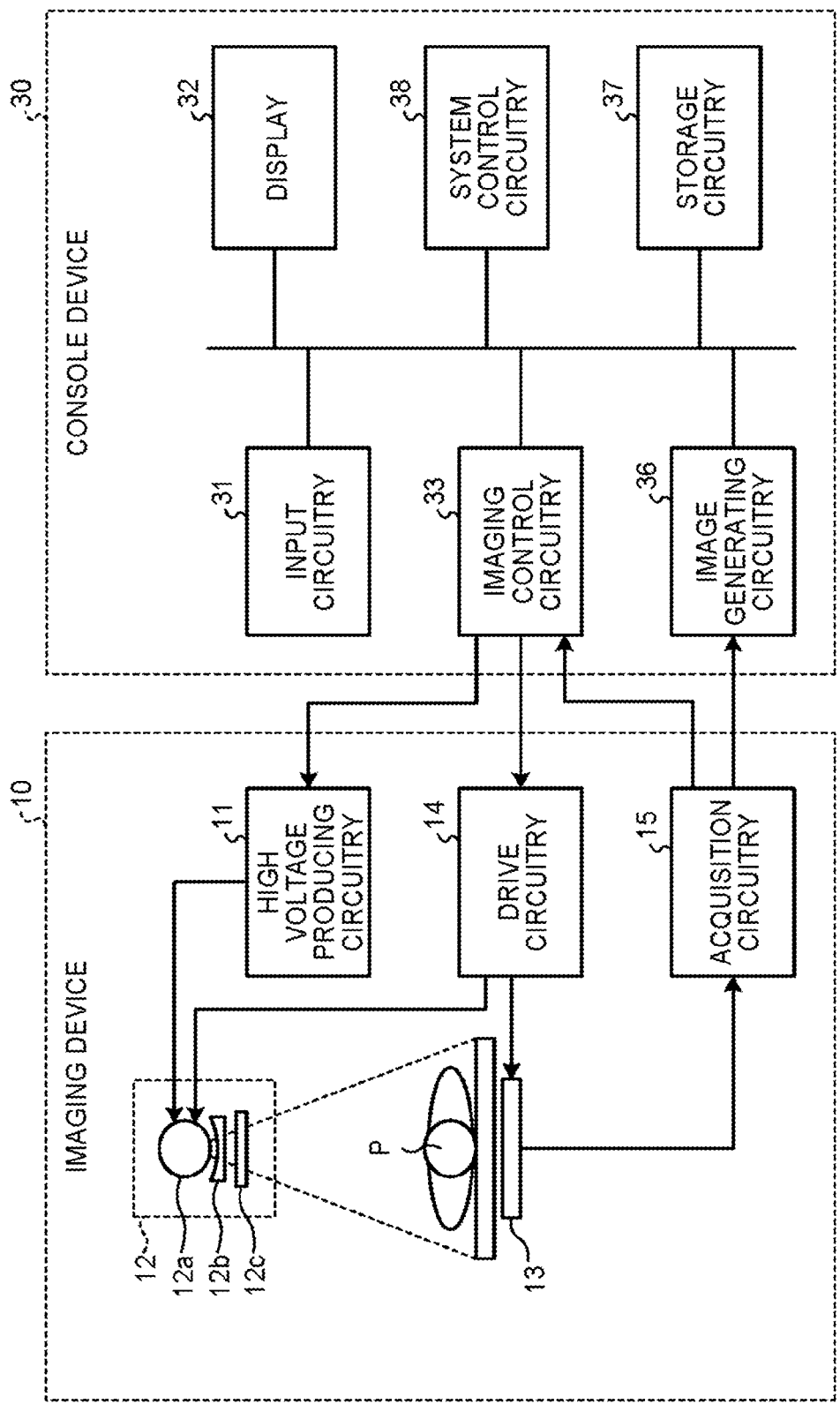
FIG. 25 is a diagram for explaining a ninth embodiment.

In the foregoing first to eighth embodiments and modifications, the apparatus that performs general radiography with an upright imaging stand, in which imaging is performed with the subject P in a standing position, has been described as an example of the X-ray diagnostic apparatus. The description in the first to eighth embodiments and modifications is applicable to an apparatus other than the X-ray diagnostic apparatus performing general radiography. FIG. 25 is a diagram for explaining a ninth embodiment, and FIG. 26 is a diagram for explaining a tenth embodiment.

FIG. 25 illustrates a configuration example of a general radiography system for upper gastrointestinal tract examination, as an X-ray diagnostic apparatus to which the description of the first to eighth embodiments and modifications is applicable. FIG. 26 illustrates a configuration example of mammography system, as an X-ray diagnostic apparatus to which the description of the first to eighth embodiments and modifications is applicable. It is noted that in FIG. 25 and FIG. 26, the processing circuitries corresponding to the plurality of processing circuitries that constitute the X-ray diagnostic apparatus illustrated in FIG. 1 are denoted by the same reference signs, for ease of explanation.

In the general radiography system for upper gastrointestinal tract examination illustrated in FIG. 25, for example, the radiation device 12 installed on the ceiling emits X-rays downward, and the detector 13 installed on the backside of the bed on which the subject P lies outputs a detection signal in response to incidence of the X-rays. In the general radiography system for upper gastrointestinal tract examination, the radiation device 12 and the bed are moved to various states, for example, from a decubitus position to an upright position and from an upright position to a decubitus position, whereby contrast-enhanced imaging of the upper gastrointestinal tract of the subject P is performed, for example. In such a configuration, the general radiography system with a decubitus imaging table illustrated in FIG. 25 performs the imaging control process described in the first to eighth embodiments and modifications, so that many target substances can be estimated with high precision, and the exposure dose can be reduced. The general radiography system with a decubitus imaging table illustrated in FIG. 25 therefore has great convenience.

Figure 26:
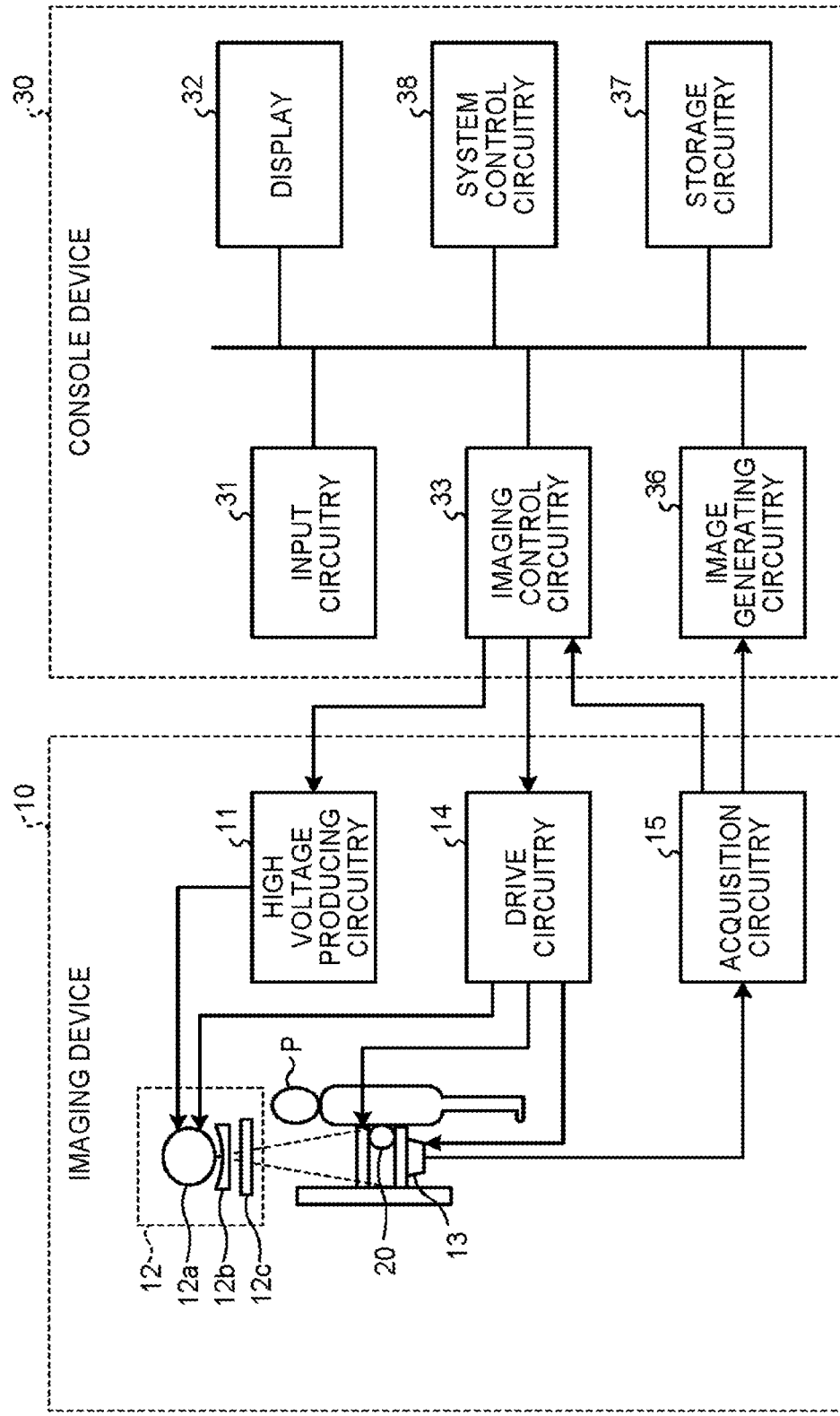
FIG. 26 is a diagram for explaining a tenth embodiment.

In the mammography system illustrated in FIG. 26, X-rays are emitted from the radiation device 12 to a breast 20 of the subject P sandwiched and expanded between the pressure plate and the imaging stand. In the mammography system illustrated in FIG. 26, the detector 13 installed on the backside of the imaging stand outputs a detection signal in response to incidence of the X-rays. In general, in the examination using mammography, each breast 20 on the right and the left is pushed on the imaging stand into a predetermined thickness, and then, for example, two images for each of the right and left breasts with different imaging directions, in total, four images are taken. In such a configuration, the mammography system illustrated in FIG. 26 performs an imaging control process described in the first to eighth embodiments and modifications, so that many target substances can be estimated with high precision, and the exposure dose can be reduced. The mammography system illustrated in FIG. 26 therefore has great convenience.

Eleventh Embodiment

In the foregoing first to tenth embodiments and modifications, the X-ray diagnostic apparatus generates an X-ray image in the form of a still image. By contrast, in an eleventh embodiment, in an X-ray diagnostic apparatus that performs X-ray fluoroscopy, a plurality of energy bins used when the acquisition circuitry 15 performs an energy bin discrimination process and X-ray radiation conditions are adaptively changed based on the respective count data of the plurality of energy bins.

As used herein, "X-ray fluoroscopy" refers to real-time imaging of the site to be observed in a time series using X-rays. The X-ray diagnostic apparatus serving as an X-ray fluoroscopic apparatus generates a plurality of still images in a time series at a plurality of imaging times and successively displays the generated still images to display moving X-ray fluoroscopic images. For example, in a case of 30 fps, the X-ray fluoroscopic apparatus takes still images of 30 frames (30 images) per second. The X-ray fluoroscopic apparatus then generates a new still image of one frame using still images of a predetermined number of frames, for example, still images of three frames.

The X-ray diagnostic apparatus in the eleventh embodiment determines a setting condition and an X-ray radiation condition for the acquisition circuitry 15 to create photon count data in the next frame, for example, based on the count data obtained in a certain frame.

Figure 27:
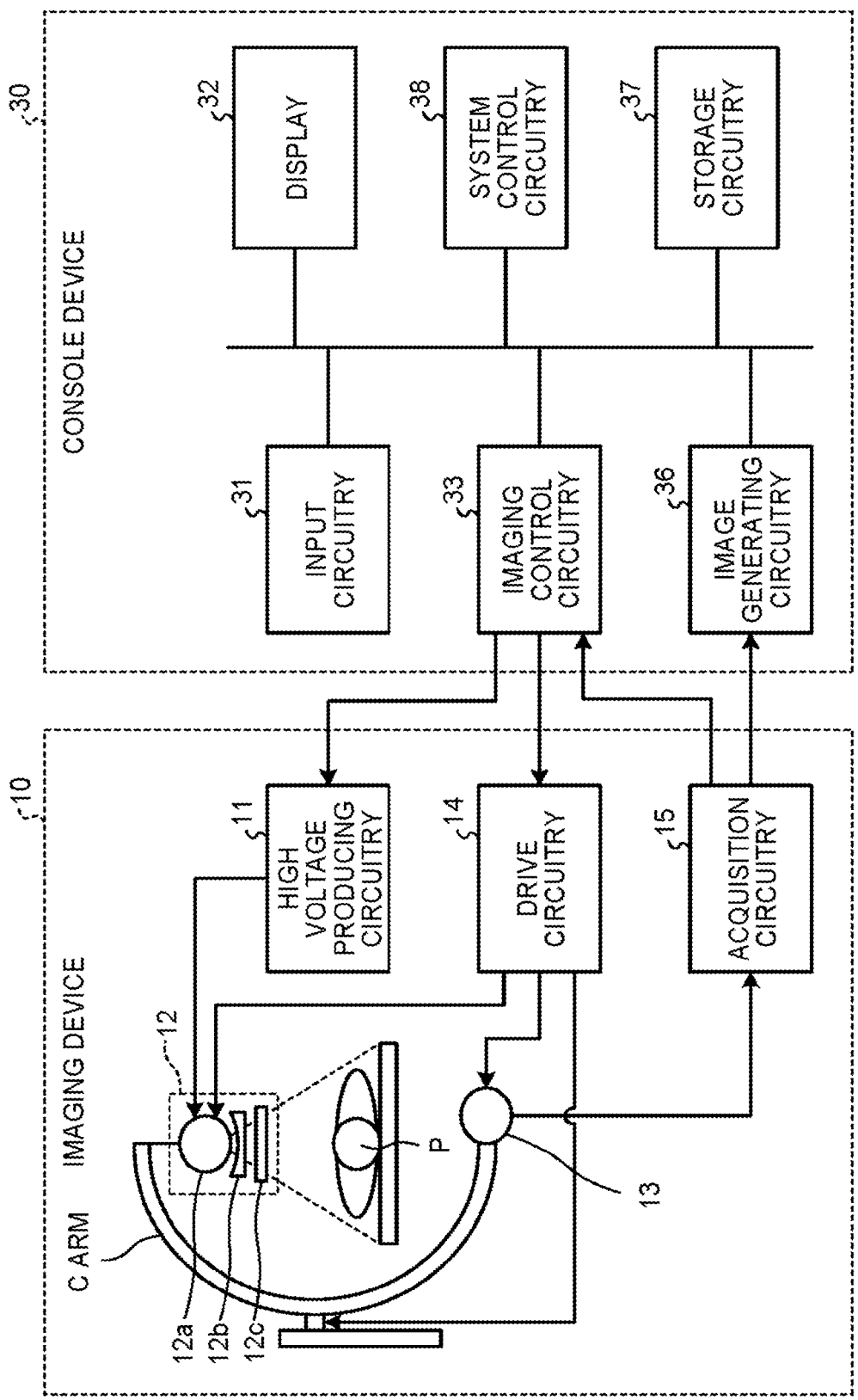
FIG. 27 is a block diagram illustrating a configuration example of the X-ray diagnostic apparatus according to an eleventh embodiment.

FIG. 27 is a block diagram illustrating a configuration example of the X-ray diagnostic apparatus according to the eleventh embodiment. It is noted that in FIG. 27, the processing circuitries corresponding to the plurality of processing circuitries that constitute the X-ray diagnostic apparatus illustrated in FIG. 1 are denoted by the same reference signs, for ease of explanation. The X-ray diagnostic apparatus illustrated in FIG. 27 is an apparatus that performs, for example, an angiographic examination and has a C arm holding the radiation device 12 and the detector 13, and the drive circuitry 14 rotates and moves the C arm. In the X-ray diagnostic apparatus illustrated in FIG. 27, the C arm is rotated and moved until the subject P lying on the bed attains an X-ray radiation angle suitable for fluoroscopy. In the X-ray diagnostic apparatus illustrated in FIG. 27, the C arm is rotated and moved to a variety of positions in a state in which the subject P is lying on the bed, whereby fluoroscopy is performed at a plurality of X-ray radiation angles.

Figure 28:
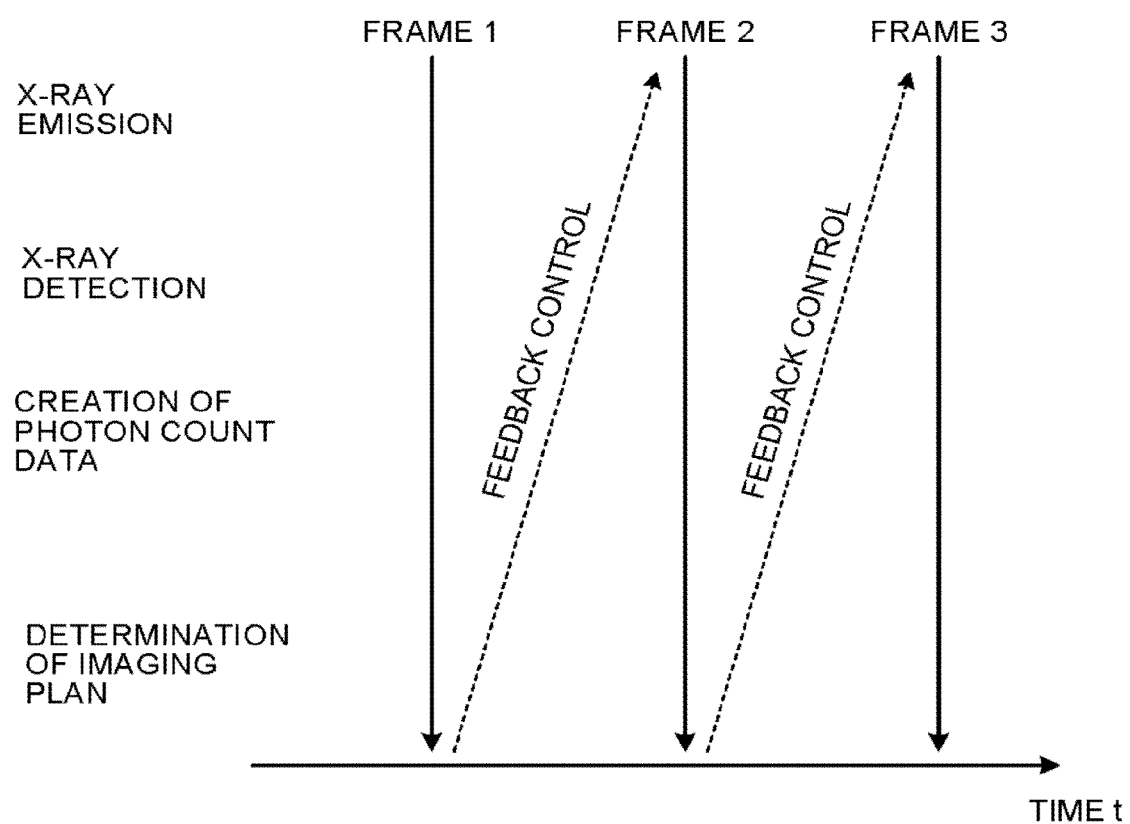
FIG. 28 is a diagram for explaining an example of the imaging control process according to the eleventh embodiment.

In such a configuration, the acquisition circuitry 15 according to the eleventh embodiment creates photon count data over a plurality of frames. The imaging control circuitry 33 according to the eleventh embodiment then determines a plurality of energy bins used when the acquisition circuitry 15 creates photon count data in imaging of the next frame, based on the photon count data created by the acquisition circuitry 15 in imaging of a certain frame. That is, the imaging control circuitry 33 determines a setting condition for allowing the acquisition circuitry 15 to set a plurality of energy bins used when the acquisition circuitry 15 creates photon count data in imaging of the next frame. The imaging control circuitry 33 determines an X-ray radiation condition in imaging of the next frame, based on the photon count data created by the acquisition circuitry 15 in imaging of a certain frame. The imaging control circuitry 33 then determines an imaging plan including the determined setting condition and X-ray radiation condition. The imaging control circuitry 33 may determine at least one of a setting condition and an X-ray radiation condition. FIG. 28 is a diagram for explaining an example of the imaging control process according to the eleventh embodiment.

FIG. 28 illustrates a still image of frame 1, a still image of frame 2, and a still image of frame 3 successively generated in a time series, where the horizontal axis represents time "t". In FIG. 28, the down arrows from frame 1, frame 2, and frame 3 each conceptually represent the process flow from X-ray radiation to generation of an image in each frame. That is, in one frame, at the first stage, X-rays are emitted to the subject P. At the second stage, the detector 13 detects the X-rays transmitted through the subject P. At the third stage, the acquisition circuitry 15 creates photon count data based on an output signal from the detector 13. At the fourth stage, the imaging control circuitry 33 determines a setting condition and an X-ray radiation condition in imaging of the next frame using photon count data and determines an imaging plan including the determined setting condition and X-ray radiation condition in the same manner as in the first embodiment. That is, the imaging control circuitry 33 determines an imaging plan in imaging of the next frame.

When X-ray radiation for one frame is finished, the image generating circuitry 36 generates one X-ray image through a material decomposition process, based on the photon count data passed from the acquisition circuitry 15. The image generating circuitry 36 then generates a new X-ray image, based on a predetermined number of X-ray images, for example, three X-ray images. The generated X-ray image is stored into the storage circuitry 37 as necessary or appears on the display 32 under the control of the system control circuitry 38.

When X-ray radiation for one frame is finished, the imaging control circuitry 33 according to the eleventh embodiment determines a setting condition and an X-ray radiation condition in imaging of the next frame, based on the photon count data passed from the acquisition circuitry 15. In the eleventh embodiment, after X-ray radiation for one frame is finished, the imaging control circuitry 33 controls the acquisition circuitry 15 so as to create photon count data using a plurality of energy bins in accordance the determined setting condition, in the next frame. The imaging control circuitry 33 controls the radiation device 12 through the high voltage producing circuitry 11 and the drive circuitry 14 so as to perform imaging in accordance with the determined X-ray radiation condition, in the next frame.

For example, as illustrated in FIG. 28, when X-ray radiation is finished in frame 1, the imaging control circuitry 33 determines a setting condition and an X-ray radiation condition in frame 2 and controls the acquisition circuitry 15 by feedback so as to create photon count data using a plurality of energy bins in accordance with the determined setting condition. The imaging control circuitry 33 also controls the radiation device 12 by feedback so as to perform imaging in accordance with the determined X-ray radiation condition. The image generating circuitry 36 generates a still image corresponding to frame 1. Next, in frame 2, X-ray radiation is started, and when X-ray radiation is subsequently finished, the imaging control circuitry 33 determines a setting condition and an X-ray radiation condition in frame 3 and controls the acquisition circuitry 15 by feedback so as to create photon count data using a plurality of energy bins in accordance with the determined setting condition. The imaging control circuitry 33 also controls the radiation device 12 by feedback so as to perform imaging in accordance with the determined X-ray radiation condition. The image generating circuitry 36 generates a still image corresponding to frame 2. This processing is repeated until the completion of imaging. The image generating circuitry 36 then generates a new still image using three still images. This still image is used in continuous shooting of X-ray fluoroscopic images.

With such processing, in the eleventh embodiment, many target substances can be estimated with high precision and the exposure dose can be reduced, even in continuous shooting of X-ray fluoroscopic images. The X-ray diagnostic apparatus according to the eleventh embodiment illustrated in FIG. 27 therefore has great convenience.

First Modification to Eleventh Embodiment

In the foregoing eleventh embodiment, the feedback control by the imaging control circuitry 33 is performed every time one frame is completed. In a first modification to the eleventh embodiment, however, the imaging control circuitry 33 determines a setting condition and an X-ray radiation condition periodically in real time during one frame, and while controlling the high voltage producing circuitry 11, the drive circuitry 14 and the acquisition circuitry 15 by feedback such that imaging is performed in accordance with the imaging plan including the determined setting condition and X-ray radiation condition, determines an imaging plan including a setting condition and an X-ray radiation condition in the next frame, upon completion of one frame. Here, any one of the methods described in the foregoing first to eighth embodiments and modifications is employed as a method by which the imaging control circuitry 33 determines a setting condition and an X-ray radiation condition periodically in real time during one frame.

In the first modification to the eleventh embodiment, in continuous shooting of X-ray fluoroscopic images, the feedback control based on count data is performed even within a frame, in addition to between frames, so that many target substances can be estimated with even higher precision, and the exposure dose can be further reduced. The X-ray diagnostic apparatus according to the first modification to the eleventh embodiment therefore has even greater convenience.

Second Modification to Eleventh Embodiment

In a second modification to the eleventh embodiment, when the X-ray radiation condition determined in a certain frame need not be changed in a plurality of subsequent successive frames (for example, three frames), the imaging control circuitry 33 determines that the optimum X-ray radiation condition has been determined, and does not perform the process of determining a setting condition and an X-ray radiation condition. On the other hand, when the setting condition and the X-ray radiation condition determined in a certain frame are successively changed, the process of determining a setting condition and an X-ray radiation condition continues.

In the second modification to the eleventh embodiment, when it is determined that the setting condition and the X-ray radiation condition are stably optimum, the imaging control circuitry 33 keeps the imaging plan including these setting condition and X-ray radiation condition and can avoid performing an unnecessary imaging control process. In the second modification to the eleventh embodiment, even when it is determined that the setting condition and the X-ray radiation condition are stably optimum, it may be determined whether the setting condition and the X-ray radiation condition need to be changed, for example, every 10 frames, and, if necessary, a setting condition and an X-ray radiation condition may be determined again.

Third Modification to Eleventh Embodiment

In a third modification to the eleventh embodiment, even when it is determined that the setting condition and the X-ray radiation condition are stably optimum, the imaging control circuitry 33 continuously determines whether the setting condition and the X-ray radiation condition need to be changed, as a background process and, if necessary, determines a setting condition and an X-ray radiation condition again. This processing enables appropriate imaging even if some event occurs at some point while a setting condition and an X-ray radiation condition are stable, and the setting condition and the X-ray radiation condition become unstable.

Twelfth Embodiment

Figure 29:
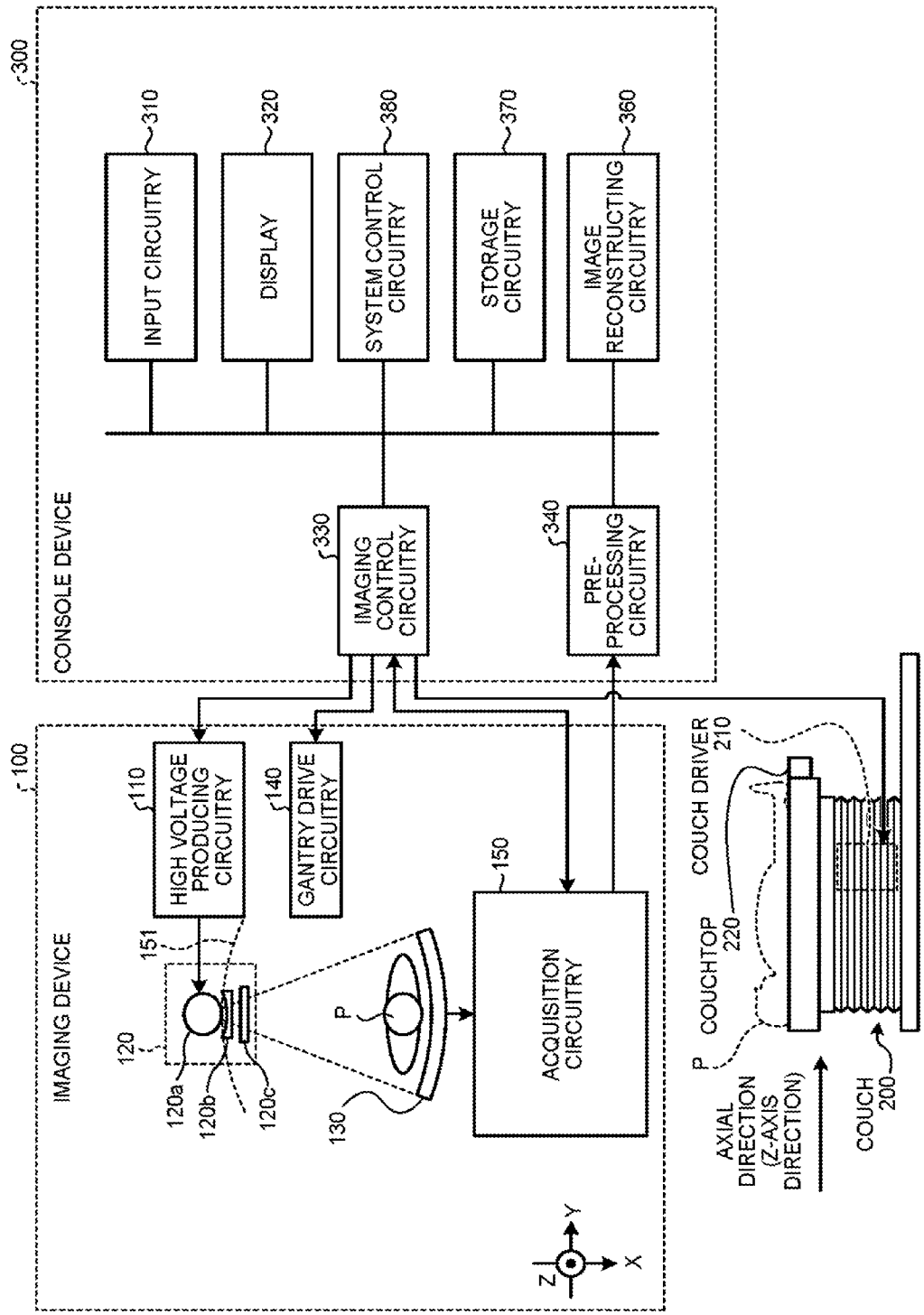
FIG. 29 is a block diagram illustrating a configuration example of an X-ray CT apparatus according to a twelfth embodiment.

In the foregoing first to eleventh embodiments and modifications, the imaging control process is performed in an X-ray diagnostic apparatus. However, the imaging control process described in the first to eleventh embodiments and modifications may be performed in an X-ray CT apparatus. FIG. 29 is a block diagram illustrating a configuration example of an X-ray CT apparatus according to a twelfth embodiment.

The X-ray CT apparatus according to the twelfth embodiment includes an imaging device 100 serving as a gantry, a couch 200, and a console device 300. The imaging device 100 includes, for example, high voltage producing circuitry 110, a radiation device 120, a detector 130, gantry drive circuitry 140, acquisition circuitry 150, and a rotary frame 151. The radiation device 120 has an X-ray tube 120a, a radiation quality filter 120b, and an X-ray beam limiting device 120c. The high voltage producing circuitry 110 corresponds to the high voltage producing circuitry 11 in FIG. 1. The radiation device 120 corresponds to the radiation device 12 in FIG. 1. The X-ray tube 120a corresponds to the X-ray tube 12a in FIG. 1. The radiation quality filter 120b corresponds to the radiation quality filter 12b in FIG. 1. The X-ray beam limiting device 120c corresponds to the X-ray beam limiting device 12c in FIG. 1. The acquisition circuitry 150 corresponds to the acquisition circuitry 15 in FIG. 1. In the X-ray CT apparatus, the radiation device 120 and the detector 130 are supported by the rotary frame 151 so as to be opposed to each other with the subject P interposed therebetween, and the rotary frame 151 is rotated fast by the gantry drive circuitry 140 on a circular orbit around the subject P.

The X-ray tube 120a emits X-rays. The detector 130 outputs a detection signal in response to incidence of the X-rays. The acquisition circuitry 150 executes an energy bin discrimination process to create photon count data indicating the number of photons for each of a plurality of energy bins.

The acquisition circuitry 150 creates photon count data in each of a plurality of tube phases (a plurality of views). Here, the acquisition circuitry 150 outputs data, for example, in the format (x,y,Count-Bin1,Count-Bin2,Count-Bin3, view) to imaging control circuitry 330 and preprocessing circuitry 340. As used herein, the "view" refers to a view obtained when X-rays are emitted. For example, a view refers to the relative positional relation between the X-ray tube 120a, the subject P, and the detector 130.

As illustrated in FIG. 29, the couch 200 is a device on which the subject P lies, and has a couchtop 220 and a couch driver 210. The couchtop 220 is a bed on which the subject P lies. The couch driver 210 moves the couchtop 220 in the Z-axis direction to move the subject P into the rotary frame 151.

As illustrated in FIG. 29, the console device 300 includes input circuitry 310, a display 320, the imaging control circuitry 330, the preprocessing circuit 340, image reconstructing circuitry 360, storage circuitry 370, and system control circuitry 380.

The input circuitry 310 and the display 320 correspond to the input circuitry 31 and the display 32, respectively, in FIG. 1. The imaging control circuitry 330 corresponds to the imaging control circuitry 33 in FIG. 1 and controls the operation of the imaging device 100 and the couch 200 under the control of the system control circuitry 380 described later to control creation of photon count data in the imaging device 100. In the twelfth embodiment, the imaging control circuitry 330 determines a setting condition in main imaging and an X-ray radiation condition in main imaging, based on the photon count data created by the acquisition circuitry 150. The imaging control circuitry 330 will be described later.

The preprocessing circuit 340 generates projection data by performing correction processing such as logarithmic transformation, offset correction, sensitivity correction, and beam hardening correction on the photon count data transmitted from the acquisition circuitry 150.

The storage circuitry 370 stores the projection data generated by the preprocessing circuit 340. That is, the storage circuitry 370 stores projection data (corrected count data) for reconstructing X-ray CT image data. The storage circuitry 370 also stores the reconstructed X-ray CT image and images generated through a variety of image processing.

The image reconstructing circuitry 360 reconstructs an image (X-ray CT image) in the imaged site using the projection data stored in the storage circuitry 370. The reconstruction method includes various methods, for example, including back projection. Examples of the back projection include back projection by the filtered back projection (FBP) method. The image reconstructing circuitry 360 may perform a reconstruction process by successive approximations. The image reconstructing circuitry 360 generates various images such as a monochrome X-ray image, a density image, and an effective atomic number image by performing a variety of image processing on an X-ray CT image or projection data before reconstruction. Examples of the image processing include material decomposition at the reconstructed image level or the projection data level. The image reconstructing circuitry 360 stores the reconstructed X-ray CT image and the images generated by a variety of image processing into the storage circuitry 370.

The system control circuitry 380 controls the overall X-ray CT apparatus by controlling the operation of the imaging device 100, the couch 200, and the console device 300. Specifically, the system control circuitry 380 controls CT scan performed in the imaging device 100 by controlling the imaging control circuitry 330. The system control circuitry 380 also controls an image reconstruction process and an image generation process in the console device 300 by controlling the preprocessing circuit 340 and the image reconstructing circuitry 360. The system control circuitry 380 also performs control such that a variety of image data stored in the storage circuitry 370 appears on the display 320.

Here, photon count data (or image) in one direction (one view) obtained in the X-ray diagnostic apparatus can be considered as projection data based on photon count data in one direction obtained in the X-ray CT apparatus. The X-ray CT apparatus takes images while gradually changing the positional relation between the X-ray tube 120a, the subject P, and the detector 130 by rotating the rotary frame 151, creates photon count data in multiple directions, and reconstructs projection data in each energy bin in multiple directions generated from the photon count data in the multiple directions, thereby generating various images.

In the X-ray CT apparatus, for example, when the rotary frame 151 makes one rotation, projection data of one frame is acquired. The initial one rotation of the rotary frame 151 from the start of imaging is hereinafter called the first cycle, and the second one rotation of the rotary frame 151 is called the second cycle. For example, in the twelfth embodiment, preliminary imaging is performed in the first cycle, and main imaging is performed in the second and subsequent cycles.

The imaging control circuitry 330 determines a setting condition concerning setting of a plurality of energy bins used when the acquisition circuitry 150 creates photon count data and an X-ray radiation condition that is a condition of X-rays emitted by the radiation device 12, in the corresponding view in the second cycle, based on photon count data created in each of a plurality of views in the first cycle. For example, the imaging control circuitry 330 determines a setting condition for setting a plurality of energy bins used when the acquisition circuitry 150 creates photon count data in view "V1" in the second cycle, based on the photon count data created in view "V1" in the first cycle. The imaging control circuitry 330 also determines an X-ray radiation condition that is a condition of X-rays emitted by the radiation device 12 in view "V1" in the second cycle, based on the photon count data created in view "V1" in the first cycle.

The imaging control circuitry 330 then controls the high voltage producing circuitry 110, the gantry drive circuitry 140, and the acquisition circuitry 150 in accordance with the imaging plan including the determined setting condition and X-ray radiation condition, in each view in the second cycle. For example, the imaging control circuitry 330 controls the acquisition circuitry 150 so as to perform main imaging in accordance with the determined setting condition, in view "V1" in the second cycle. The imaging control circuitry 330 also controls the high voltage producing circuitry 110 so as to perform main imaging in accordance with the determined X-ray radiation condition, in view "V1" in the second cycle. The imaging control circuitry 330 repeats the control described above in all of the views or at least one view in the second and subsequent cycles until shooting of X-ray CT images is finished. The image reconstructing circuitry 360 thus reconstructs an image in which four target substances "Iodine", "Gadolinium", "Bone", and "Platinum" are identified.

Figure 30A:
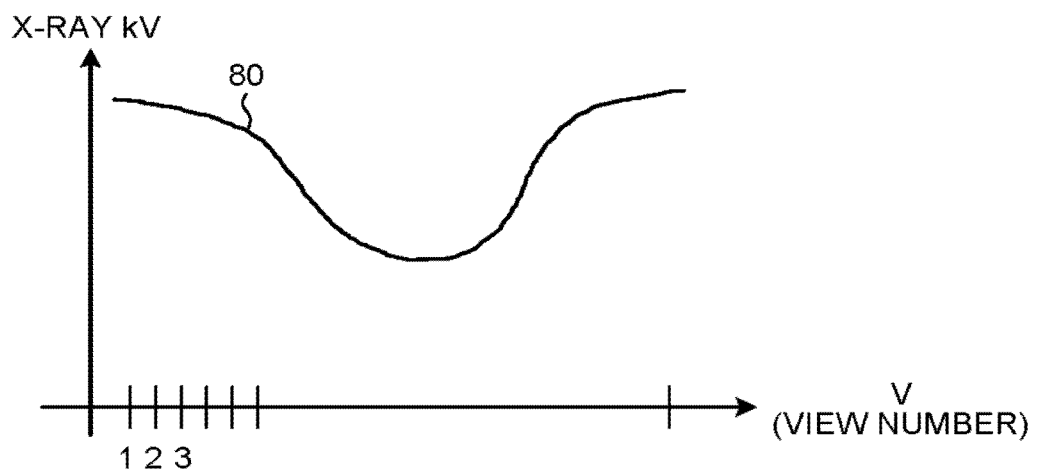
FIG. 30A is a diagram for explaining an example of the process executed by the X-ray CT apparatus according to the twelfth embodiment.
Figure 30B:
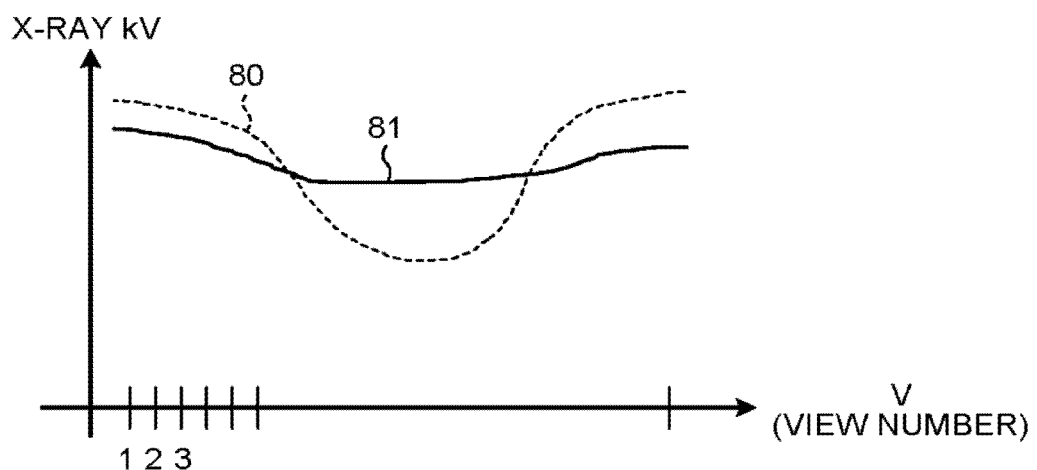
FIG. 30B is a diagram for explaining an example of the process executed by the X-ray CT apparatus according to the twelfth embodiment.

The imaging control circuitry 330 may determine a setting condition and an X-ray radiation condition in the second cycle, using a statistical value (for example, minimum value, maximum value, average, median value) of the count value of photons in each energy bin in each of a plurality of views obtained in the first cycle or a statistical value of the count value of photons per unit time. Alternatively, the imaging control circuitry 330 may determine a setting condition and an X-ray radiation condition in each view in the second cycle, using the count value of photons in each energy bin in each of a plurality of views obtained in the first cycle or a statistical value of the count value of photons per unit time. FIGS. 30A and 30B are diagrams for explaining an example of the process executed by the X-ray CT apparatus according to the twelfth embodiment. FIGS. 30A and 30B illustrate graphs in which the horizontal axis represents views and the vertical axis represents tube voltage. FIG. 30A illustrates a graph 80 representing the magnitude of tube voltage in each view in the first cycle. FIG. 30B illustrates a graph 81 representing the magnitude of tube voltage in each view in the second cycle, in addition to the graph 80. For example, the imaging control circuitry 330 controls the X-ray tube 12a such that the magnitude of tube voltage in each view reaches the magnitude of tube voltage in each view illustrated by the graph 80 in FIG. 30A, in the first cycle. The imaging control circuitry 330 then controls the X-ray tube 12a such that the magnitude of tube voltage in each view reaches the magnitude of tube voltage in each view illustrated by the graph 81 in FIG. 30B, in the second cycle, based on the count value of photons in each energy bin in each of a plurality of views obtained in the first cycle. The imaging control circuitry 330 repeats the processing above until shooting of X-ray CT images is finished.

The imaging control circuitry 330 can also control the movement of the couchtop 220 in the Z-axis direction in the next cycle, based on the average of the count values of photons in each energy bin in each of a plurality of views obtained in a certain cycle. For example, the imaging control circuitry 330 calculates, for each view, the amount of movement of the couchtop 220 in the Z-axis direction in the next cycle, based on the average of the count values of photons in each energy bin in each of a plurality of views obtained in a certain cycle and determines, for each view, an X-ray radiation condition for moving the couchtop 220 in the Z-axis direction by the calculated amount of movement. The imaging control circuitry 330 then controls the couch driver 210 in accordance with the corresponding X-ray radiation condition in each of a plurality of views in the next cycle. The couch driver 210 thus moves the couchtop 220 in the Z-axis direction by the calculated amount of movement.

In this manner, in the twelfth embodiment, the X-ray CT apparatus executes the imaging control process described in the first to eleventh embodiments and modifications, so that many target substances can be estimated with high precision also in photon-counting CT. According to the twelfth embodiment, the exposure dose can be reduced as in the first to eleventh embodiments and modifications. The X-ray CT apparatus according to the twelfth embodiment therefore has great convenience.

Thirteenth Embodiment

The imaging control process described in the first to eleventh embodiments and modifications may be executed by a dual energy X-ray CT apparatus. Such an embodiment will now be described as a thirteenth embodiment. A dual energy X-ray CT apparatus switches between two energies of X-rays emitted from the X-ray tube, for each cycle (for example, 140 [keV] in the first cycle, 80 [keV] in the second cycle) and combines the spectra of different energies to generate a sinogram. The dual energy X-ray CT apparatus performs the imaging control process in the same manner as in the first to eleventh embodiments and modifications, in which the output of the acquisition circuitry when X-rays having the higher energy between the two energies are emitted from the X-ray tube is considered as the count value of photons in an energy bin with high energy, and the output of the acquisition circuitry when X-rays having the lower energy are emitted from the X-ray tube is considered as the count value of photons in an energy bin with low energy.

According to the thirteenth embodiment, many target substances can be estimated with high precision, and the exposure dose can be reduced, as in the first to twelfth embodiments and modifications. The dual energy X-ray CT apparatus according to the thirteenth embodiment therefore has great convenience.

It is noted that the components of the devices illustrated in the accompanying drawings are functional and conceptual and not necessarily physically configured as illustrated in the drawings. That is, specific manners of distribution and integration of the devices are not intended to be limited to those illustrated in the drawings, and all or some of them may be functionally or physically distributed or integrated in any given unit depending on loads and use conditions. The processing function performed in each device may be entirely or partially implemented by a CPU and a program analyzed and executed by the CPU or may be implemented by hardware with wired logic.

A variety of methods described in the first to thirteenth embodiments and modifications can be implemented by a control program prepared in advance and running on a computer such as a personal computer or a workstation. This control program may be distributed over a network such as the Internet. Alternatively, the control program may be recorded on a non-transitory computer-readable recording medium such as a hard disk, a flexible disk (FD), a compact disc-read-only memory (CD-ROM), a magneto-optical disk (MO), or a digital versatile disc (DVD), and read out from the recording medium by a computer for execution.

At least one of the embodiments and the modifications as described above provides great convenience.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray tube configured to emit X-rays to a subject;
a detector configured to output a detection signal in response to incidence of the X-rays passed through the subject;
acquisition circuitry configured to create photon count data indicating the number of photons of the X-rays incident on the detector, for each of a plurality of energy bins for identifying a plurality of target substances, based on the detection signal output by the detector;

imaging control circuitry configured to determine, based on the photon count data created by the acquisition circuitry or image data of the subject, an imaging plan including at least one of a setting condition which is a condition concerning setting of the plurality of energy bins used upon creation of photon count data by the acquisition circuitry in main imaging and an X-ray radiation condition which is a condition concerning the X-rays emitted by the X-ray tube in the main imaging, and to control such that the main imaging is performed in accordance with the determined imaging plan.

2. The X-ray diagnostic apparatus according to claim 1, wherein the imaging control circuitry controls the acquisition circuitry and the X-ray tube such that the main imaging is performed in accordance with the imaging plan including the setting condition and the X-ray radiation condition.

3. The X-ray diagnostic apparatus according to claim 1, wherein in preliminary imaging performed prior to the main imaging, the imaging control circuitry determines the imaging plan in accordance with the photon count data created by the acquisition circuitry, and controls such that the main imaging is performed in accordance with the determined imaging plan.

4. The X-ray diagnostic apparatus according to claim 1, wherein during the main imaging performed in accordance with the determined imaging plan, the imaging control circuitry updates the imaging plan in accordance with the photon count data created by the acquisition circuitry, and controls such that the main imaging is performed in accordance with the updated imaging plan.

5. The X-ray diagnostic apparatus according to claim 1, wherein the imaging control circuitry estimates the photon count data based on the image data, determines the imaging plan based on the estimated photon count data, and controls such that the main imaging is performed in accordance with the determined imaging plan.

6. The X-ray diagnostic apparatus according to claim 1, wherein the imaging control circuitry:

controls the acquisition circuitry such that first photon count data indicating the number of photons of the X-rays incident on the detector is created for each of a first plurality of energy bins for identifying a predetermined plurality of target substances; and determines the imaging plan including the setting condition for switching the first plurality of energy bins to a second plurality of energy bins different from the first plurality of energy bins in width of at least one energy bin, in accordance with a result of comparison of the number of photons for each of the first plurality of energy bins indicated by the first photon count data with a corresponding predetermined threshold; and in the main imaging, in accordance with the imaging plan, controls the acquisition circuitry so as to switch the first plurality of energy bins to the second plurality of energy bins; and controls the acquisition circuitry so as to create second photon count data indicating the number of photons of the X-rays incident on the detector, for each of the switched second plurality of energy bins.

7. The X-ray diagnostic apparatus according to claim 6, wherein when the number of photons for each of the first plurality of energy bins exceeds a corresponding predetermined threshold, the imaging control circuitry:

determines the imaging plan including the setting condition for switching the first plurality of energy bins to the second plurality of energy bins for identifying another target substance other than the predetermined target substances; and in the main imaging, in accordance with the imaging plan, controls the acquisition circuitry so as to switch the first plurality of energy bins to the second plurality of energy bins; and controls the acquisition circuitry so as to create the second photon count data.

8. The X-ray diagnostic apparatus according to claim 6, wherein when the first plurality of energy bins include an energy bin in which the number of photons does not exceed a corresponding predetermined threshold, the imaging control circuitry:

determines the imaging plan including the setting condition for switching the first plurality of energy bins to the second plurality of energy bins including the energy bin not exceeding the corresponding predetermined threshold; and in the imaging, in accordance with the imaging plan, controls the acquisition circuitry so as to switch the first plurality of energy bins to the second plurality of energy bins; and controls the acquisition circuitry so as to create the second photon count data.

9. The X-ray diagnostic apparatus according to claim 6, wherein when the first plurality of energy bins include an energy bin in which the number of photons does not exceed a corresponding predetermined threshold, the imaging control circuitry:

determines the imaging plan including the setting condition for switching the first plurality of energy bins to the second plurality of energy bins; and in the main imaging, in accordance with the imaging plan, controls the acquisition circuitry so as to switch the first plurality of energy bins to the second plurality of energy bins;

controls the acquisition circuitry so as to create the second photon count data; and calculates the number of photons in the energy bin not exceeding the corresponding predetermined threshold, based on the first photon count data and the second photon count data created by the acquisition circuitry.

10. The X-ray diagnostic apparatus according to claim 6, wherein when the first plurality of energy bins include an energy bin in which the number of photons does not exceed another threshold smaller than the corresponding predetermined threshold, the imaging control circuitry:

determines the imaging plan including the setting condition for switching the first plurality of energy bins to a new second plurality of energy bins in which a width of the energy bin in which the number of photons does not exceed the another threshold is increased; and in the main imaging, in accordance with the imaging plan, controls the acquisition circuitry so as to switch the first plurality of energy bins to the new second plurality of energy bins; and controls the acquisition circuitry so as to create second photon count data indicating the number of photons of the X-rays incident on the detector for each of the switched new second plurality of energy bins.

11. The X-ray diagnostic apparatus according to claim 1, wherein the imaging control circuitry:

controls the acquisition circuitry such that first photon count data indicating the number of photons of the X-rays incident on the detector is created for each of a first plurality of energy bins for identifying a predetermined plurality of target substances; and determines the imaging plan including the setting condition for switching the first plurality of energy bins to a second plurality of energy bins different from the first plurality of energy bins in width of at least one energy bin, in accordance with a result of comparison of noise components for each of the first plurality of energy bins determined from the number of photons for each of the first plurality of energy bins indicated by the first photon count data with a corresponding predetermined threshold; and in the main imaging, in accordance with the imaging plan,
controls the acquisition circuitry so as to switch the first plurality of energy bins to the second plurality of energy bins; and
controls the acquisition circuitry so as to create second photon count data indicating the number of photons of the X-rays incident on the detector, for each of the switched second plurality of energy bins.

12. The X-ray diagnostic apparatus according to claim 1, wherein
the acquisition circuitry creates photon count data indicating the number of photons of the X-rays incident on the detector, for each of the plurality of energy bins, over a plurality of frames, and
the imaging control circuitry determines the imaging plan for the acquisition circuitry to next time create the photon count data, based on the photon count data created by the acquisition circuitry.

13. The X-ray diagnostic apparatus according to claim 1, wherein the imaging control circuitry determines the imaging plan including the X-ray radiation condition concerning voltage of the X-ray tube.

14. The X-ray diagnostic apparatus according to claim 1, wherein the imaging control circuitry determines the imaging plan including the X-ray radiation condition concerning current of the X-ray tube.

15. The X-ray diagnostic apparatus according to claim 1, wherein the imaging control circuitry determines the imaging plan including the X-ray radiation condition concerning control on a radiation quality filter for the X-ray tube.

16. The X-ray diagnostic apparatus according to claim 1, wherein the imaging control circuitry determines the imaging plan including the X-ray radiation condition concerning an X-ray beam limiter.

17. The X-ray diagnostic apparatus according to claim 1, wherein the imaging control circuitry determines the imaging plan including the X-ray radiation condition concerning exposure adjustment control on the X-rays.

18. The X-ray diagnostic apparatus according to claim 17, wherein the exposure adjustment control is control of controlling the X-ray tube so as to emit the X-rays for a preset radiation time or control of controlling the X-ray tube, based on an electrical signal indicating an incident X-ray dose obtained by a detector for exposure adjustment, so as to stop radiation of the X-rays when the incident X-ray dose indicated by the electrical signal reaches a predetermined value.

19. The X-ray diagnostic apparatus according to claim 1, further comprising drive circuitry configured to control a position of the detector, wherein
the imaging control circuitry determines the imaging plan including a condition concerning a position of the detector, and controls the drive circuitry in the main imaging in accordance with the determined imaging plan.

20. The X-ray diagnostic apparatus according to claim 1, wherein the imaging control circuitry determines the X-ray radiation condition by using a parameter linked to a radiation plan for the subject, and determines the imaging plan including the determined X-ray radiation condition.

21. The X-ray diagnostic apparatus according to claim 20, wherein the imaging control circuitry:
determines the X-ray radiation condition by using the parameter linked to the radiation plan according to a site to be imaged, a substance of interest, or an individual difference of the subject; and
determines the imaging plan including the determined X-ray radiation condition.

22. The X-ray diagnostic apparatus according to claim 1, wherein the imaging control circuitry determines the imaging plan in accordance with the number of photons of the X-rays for each of the plurality of energy bins or the number of photons of the X-rays per unit time for each of the plurality of energy bins.

23. The X-ray diagnostic apparatus according to claim 1, wherein the imaging control circuitry determines the imaging plan in accordance with the number of photons of the X-rays for each of the plurality of energy bins in each of a plurality of regions of interest or a sum of the number of photons of the X-rays for each of the plurality of energy bins in each of a plurality of regions of interest.

24. The X-ray diagnostic apparatus according to claim 1, wherein the imaging control circuitry determines the imaging plan including two or more kinds of the X-ray radiation condition.

25. The X-ray diagnostic apparatus according to claim 1, wherein the imaging control circuitry changes a control amount to be included in the X-ray radiation condition in accordance with the photon count data.

26. The X-ray diagnostic apparatus according to claim 1, wherein the imaging control circuitry changes a parameter to be used in determining the imaging plan in accordance with the photon count data.

27. The X-ray diagnostic apparatus according to claim 1, wherein the imaging control circuitry stores a history of the imaging plan into storage circuitry.

28. An X-ray computed tomography (CT) apparatus comprising:
an X-ray tube configured to repeatedly emit X-rays to a subject in each of a plurality of views;
a detector configured to output a detection signal in each of the plurality of views in response to incidence of the X-rays passed through the subject;
acquisition circuitry configured to create photon count data for each view in accordance with the detection signal output from the detector, the photon count data indicating the number of photons of the X-rays incident on the detector for each of a plurality of energy bins;
imaging control circuitry configured to determine, in accordance with the photon count data in a certain view created by the acquisition circuitry, an imaging plan including at least one of a setting condition which is a condition concerning setting of the plurality of energy bins used upon creation of photon count data by the acquisition circuitry in the certain view in the main imaging and an X-ray radiation condition which is a condition of the X-rays emitted by the X-ray tube in the certain view in the main imaging, and to control such that the main imaging is performed in the certain view in accordance with the determined imaging plan.

29. The X-ray CT apparatus according to claim 28, further comprising couch driving circuitry configured to control a position of a couch on which the subject lies, wherein
the imaging control circuitry determines the imaging plan including a condition concerning the position of the couch.

* * * * *